US008694080B2

(12) United States Patent
Farrior

(10) Patent No.: US 8,694,080 B2
(45) Date of Patent: Apr. 8, 2014

(54) ECG LEAD SYSTEM

(75) Inventor: Justin Farrior, Pensacola, FL (US)

(73) Assignee: Covidien LP, Mansfield, MA (US)

( * ) Notice: Subject to any disclaimer, the term of this patent is extended or adjusted under 35 U.S.C. 154(b) by 40 days.

(21) Appl. No.: 12/876,316

(22) Filed: Sep. 7, 2010

(65) Prior Publication Data
US 2011/0092833 A1  Apr. 21, 2011

Related U.S. Application Data

(60) Provisional application No. 61/289,144, filed on Dec. 22, 2009, provisional application No. 61/253,556, filed on Oct. 21, 2009.

(51) Int. Cl.
*A61B 5/0402* (2006.01)

(52) U.S. Cl.
USPC ........................................ 600/509; 600/508

(58) Field of Classification Search
USPC .............................. 607/60; 600/418, 508, 509
See application file for complete search history.

(56) References Cited

U.S. PATENT DOCUMENTS

| 3,606,881 A | 9/1971 | R.D. Woodson |
| 3,752,151 A | 8/1973 | Robichaud |
| 3,805,769 A | 4/1974 | Sessions |
| 3,828,766 A | 8/1974 | Krasnow |
| 3,868,946 A | 3/1975 | Hurley |
| 3,888,240 A | 6/1975 | Reinhold, Jr. et al. |
| 3,895,635 A | 7/1975 | Justus et al. |
| 3,901,218 A | 8/1975 | Buchalter |
| 3,997,225 A * | 12/1976 | Horwinski ............... 439/105 |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,112,941 A | 9/1978 | Larimore |
| 4,166,465 A | 9/1979 | Esty et al. |
| 4,353,372 A | 10/1982 | Ayer |
| 4,365,634 A | 12/1982 | Bare et al. |
| 4,498,480 A | 2/1985 | Mortensen |

(Continued)

FOREIGN PATENT DOCUMENTS

| DE | 90 02 539 U1 | 5/1990 |
| DE | 9002539 U1 | 5/1990 |

(Continued)

OTHER PUBLICATIONS

European Search Report corresponding to European Application No. EP 07 25 3850, date of completion is Dec. 21, 2007; 2 pages.

(Continued)

*Primary Examiner* — Christopher D Koharski
*Assistant Examiner* — Michael Carey
(74) *Attorney, Agent, or Firm* — Lisa E. Winsor, Esq.

(57) ABSTRACT

An ECG lead system for use with a plurality of unique diverse ECG floor monitors for when a patient is substantially immobile and/or a plurality of unique diverse ECG telemetry monitors, is provided. The ECG lead system includes a plurality of unique adapters, wherein each adapter includes an input receptacle configured for selective electrical connection with a device connector of an ECG lead set assembly; and at least one unique monitor plug electrically connected to the input receptacle. Each monitor plug is configured to selectively electrically connect to a corresponding receptacle of a respective unique diverse ECG floor monitor or unique diverse ECG telemetry monitor.

18 Claims, 26 Drawing Sheets

(56) References Cited

U.S. PATENT DOCUMENTS

| | | |
|---|---|---|
| 4,729,377 A | 3/1988 | Granek et al. |
| 4,763,660 A | 8/1988 | Kroll et al. |
| 4,781,200 A | 11/1988 | Baker |
| 4,785,822 A | 11/1988 | Wallace |
| 4,815,964 A | 3/1989 | Cohen et al. |
| 4,850,356 A * | 7/1989 | Heath .......................... 607/142 |
| 4,909,260 A | 3/1990 | Salem et al. |
| 4,947,846 A | 8/1990 | Kitagawa et al. |
| 4,957,109 A | 9/1990 | Groeger et al. |
| 5,080,604 A | 1/1992 | Rider et al. |
| 5,083,238 A | 1/1992 | Bousman |
| 5,083,933 A | 1/1992 | Colleran et al. |
| 5,104,253 A | 4/1992 | Zielinski et al. |
| 5,104,334 A | 4/1992 | Honma et al. |
| 5,131,854 A | 7/1992 | Jose et al. |
| 5,137,466 A | 8/1992 | Endo et al. |
| 5,154,646 A | 10/1992 | Shoup |
| 5,158,469 A | 10/1992 | Martin |
| 5,160,276 A | 11/1992 | Marsh et al. |
| 5,173,059 A | 12/1992 | Sato et al. |
| 5,176,343 A | 1/1993 | Cheney et al. |
| 5,178,556 A | 1/1993 | Chen |
| 5,180,312 A | 1/1993 | Martin |
| 5,190,467 A | 3/1993 | Ohta |
| 5,192,226 A | 3/1993 | Wang |
| 5,197,901 A | 3/1993 | Hashiguchi |
| 5,199,897 A | 4/1993 | Hashiguchi |
| 5,201,669 A | 4/1993 | Lin |
| 5,203,715 A | 4/1993 | Yamamoto |
| 5,203,719 A | 4/1993 | Kozono |
| 5,207,594 A * | 5/1993 | Olson .......................... 439/490 |
| 5,224,479 A | 7/1993 | Sekine |
| 5,232,383 A | 8/1993 | Barnick |
| 5,234,357 A | 8/1993 | Yamaguchi |
| 5,243,510 A | 9/1993 | Cheney |
| 5,263,481 A | 11/1993 | Axelgaard |
| 5,276,443 A | 1/1994 | Gates et al. |
| 5,278,759 A | 1/1994 | Berra et al. |
| 5,293,013 A | 3/1994 | Takahashi |
| 5,320,621 A | 6/1994 | Gordon et al. |
| 5,326,272 A | 7/1994 | Harhen et al. |
| 5,332,330 A | 7/1994 | Kaneko |
| 5,338,219 A | 8/1994 | Hiramoto |
| 5,341,806 A | 8/1994 | Gadsby et al. |
| 5,341,812 A * | 8/1994 | Allaire et al. ................. 600/508 |
| 5,353,793 A | 10/1994 | Bornn |
| 5,362,249 A | 11/1994 | Carter |
| 5,370,116 A | 12/1994 | Rollman et al. |
| 5,370,550 A | 12/1994 | Alwine et al. |
| 5,376,016 A | 12/1994 | Inaba et al. |
| 5,378,168 A | 1/1995 | Sumida |
| 5,380,223 A | 1/1995 | Marsh et al. |
| 5,382,176 A | 1/1995 | Norden |
| 5,383,794 A | 1/1995 | Davis et al. |
| 5,387,116 A | 2/1995 | Wang |
| 5,387,127 A | 2/1995 | Wang |
| 5,399,045 A | 3/1995 | Yoneda et al. |
| 5,405,269 A | 4/1995 | Stupecky |
| 5,415,164 A | 5/1995 | Faupel et al. |
| 5,429,526 A | 7/1995 | Ann |
| 5,454,739 A | 10/1995 | Strand |
| 5,462,448 A | 10/1995 | Kida et al. |
| 5,486,117 A | 1/1996 | Chang |
| 5,507,290 A | 4/1996 | Kelly et al. |
| 5,507,665 A | 4/1996 | Oda |
| 5,507,668 A | 4/1996 | Lambrinos et al. |
| 5,509,822 A | 4/1996 | Negus et al. |
| 5,511,553 A | 4/1996 | Segalowitz |
| 5,546,950 A | 8/1996 | Schoeckert et al. |
| 5,558,535 A | 9/1996 | Saka et al. |
| 5,564,939 A | 10/1996 | Maitani et al. |
| 5,582,180 A | 12/1996 | Manset et al. |
| 5,584,719 A | 12/1996 | Tsuji et al. |
| 5,599,199 A | 2/1997 | Wright |
| 5,603,632 A | 2/1997 | Johannes et al. |
| 5,611,708 A | 3/1997 | Mizunuma et al. |
| 5,613,870 A | 3/1997 | Traver, Jr. |
| 5,615,674 A | 4/1997 | Maurer |
| 5,622,168 A | 4/1997 | Keusch et al. |
| 5,624,271 A | 4/1997 | Childs et al. |
| 5,626,135 A | 5/1997 | Sanfilippo |
| 5,632,274 A | 5/1997 | Quedens et al. |
| 5,651,689 A | 7/1997 | Plyler et al. |
| 5,653,606 A | 8/1997 | Chrysostomou |
| 5,674,088 A | 10/1997 | Roche et al. |
| 5,676,694 A | 10/1997 | Boser et al. |
| 5,679,022 A | 10/1997 | Cappa et al. |
| 5,679,029 A | 10/1997 | Saunier et al. |
| 5,685,303 A | 11/1997 | Rollman et al. |
| 5,695,355 A | 12/1997 | Hasenfratz et al. |
| 5,702,265 A | 12/1997 | Yamaguchi |
| 5,704,351 A | 1/1998 | Mortara et al. |
| 5,711,684 A | 1/1998 | Inoue et al. |
| 5,718,596 A | 2/1998 | Inaba et al. |
| 5,724,025 A | 3/1998 | Tavori |
| 5,724,984 A | 3/1998 | Arnold et al. |
| 5,725,525 A | 3/1998 | Kordis |
| 5,741,155 A | 4/1998 | Herman |
| 5,749,746 A | 5/1998 | Tan et al. |
| 5,769,650 A | 6/1998 | Aoyama et al. |
| 5,772,591 A | 6/1998 | Cram |
| 5,775,953 A | 7/1998 | Yamanashi et al. |
| 5,782,647 A | 7/1998 | Okura et al. |
| 5,782,892 A | 7/1998 | Castle et al. |
| 5,788,527 A | 8/1998 | Sanders et al. |
| 5,797,854 A | 8/1998 | Hedgecock |
| 5,806,152 A | 9/1998 | Saitou et al. |
| 5,813,404 A | 9/1998 | Devlin et al. |
| 5,813,979 A | 9/1998 | Wolfer |
| 5,827,086 A | 10/1998 | Fukuda |
| 5,830,000 A | 11/1998 | Shifflett et al. |
| 5,836,783 A | 11/1998 | Morisawa et al. |
| 5,843,141 A | 12/1998 | Bischoff et al. |
| 5,848,456 A | 12/1998 | Sjoqvist |
| 5,865,740 A | 2/1999 | Kelly et al. |
| 5,865,741 A | 2/1999 | Kelly et al. |
| 5,871,451 A | 2/1999 | Unger et al. |
| 5,873,747 A | 2/1999 | Tsuji |
| 5,876,232 A | 3/1999 | Matsushita et al. |
| 5,895,284 A | 4/1999 | Kocher et al. |
| 5,904,579 A | 5/1999 | McLean et al. |
| 5,913,834 A | 6/1999 | Francais |
| 5,916,159 A | 6/1999 | Kelly et al. |
| 5,931,689 A | 8/1999 | Patel |
| 5,931,861 A | 8/1999 | Werner et al. |
| 5,934,926 A | 8/1999 | Gabrisko, Jr. et al. |
| 5,937,950 A | 8/1999 | Adams et al. |
| 5,938,470 A | 8/1999 | Kashiyama |
| 5,938,597 A | 8/1999 | Stratbucker |
| 5,941,725 A | 8/1999 | Brennan et al. |
| 5,951,316 A | 9/1999 | Kawano et al. |
| 5,964,624 A | 10/1999 | Pernelle |
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,006,125 A | 12/1999 | Kelly et al. |
| 6,027,359 A | 2/2000 | Aoki et al. |
| 6,032,063 A | 2/2000 | Hoar et al. |
| 6,032,064 A | 2/2000 | Devlin et al. |
| 6,038,479 A | 3/2000 | Werner et al. |
| 6,038,481 A | 3/2000 | Werner et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |

(56) References Cited

U.S. PATENT DOCUMENTS

| | | | |
|---|---|---|---|
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,190,385 B1 | 2/2001 | Tom et al. |
| 6,203,354 B1 | 3/2001 | Kuwahara et al. |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky et al. |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,324,432 B1 | 11/2001 | Rigaux et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,447,170 B1 | 9/2002 | Takahashi et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisandier |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B1 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wi |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 * | 8/2004 | Schwarz ............... 439/725 |
| 6,786,755 B2 | 9/2004 | Dambach et al. |
| 6,786,764 B2 | 9/2004 | Sivertsen |
| 6,816,744 B2 | 11/2004 | Garfield et al. |
| 6,832,928 B2 | 12/2004 | Suzuki et al. |
| 6,837,734 B2 | 1/2005 | Ushio et al. |
| 6,847,836 B1 | 1/2005 | Sujdak |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | Knight et al. |
| 6,945,796 B2 | 9/2005 | Bassler et al. |
| 6,945,807 B1 | 9/2005 | Wu |
| 6,948,973 B1 * | 9/2005 | Hsu et al. ............... 439/495 |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 6,984,143 B2 | 1/2006 | Roese |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,081,008 B2 | 7/2006 | Tan |
| 7,085,598 B2 | 8/2006 | Sato |
| 7,104,801 B1 | 9/2006 | Brodnick et al. |

(56) References Cited

U.S. PATENT DOCUMENTS

| | | |
|---|---|---|
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,150,655 B2 | 12/2006 | Mastrototaro et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | Le Gallic et al. |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,258,565 B2 | 8/2007 | Huang et al. |
| 7,258,566 B2 | 8/2007 | Koenig et al. |
| 7,264,510 B2 | 9/2007 | Koenig et al. |
| 7,270,568 B2 | 9/2007 | Osypka |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillinville et al. |
| 7,322,849 B2 | 1/2008 | Sutton |
| 7,329,139 B2 | 2/2008 | Benham |
| 7,333,850 B2 | 2/2008 | Marossero et al. |
| 7,347,710 B2 | 3/2008 | Ohtaka et al. |
| 7,347,826 B1 | 3/2008 | Karicherla et al. |
| 7,359,751 B1 | 4/2008 | Erickson et al. |
| 7,361,058 B1 | 4/2008 | Lien et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 * | 7/2008 | Okada et al. ............... 439/248 |
| 7,399,195 B2 | 7/2008 | Kim et al. |
| 7,401,946 B2 | 7/2008 | Laukhuf |
| 7,402,071 B2 * | 7/2008 | Ohtaka et al. ............... 439/357 |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achter et al. |
| 7,462,074 B1 | 12/2008 | Devlin et al. |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| 7,666,028 B2 | 2/2010 | Meleck |
| 8,038,484 B2 | 10/2011 | Selvitelli et al. |
| 8,255,041 B2 * | 8/2012 | Istvan et al. ............... 600/509 |
| 2002/0133069 A1 | 9/2002 | Roberts |
| 2002/0138011 A1 | 9/2002 | Rantala |
| 2002/0188216 A1 | 12/2002 | Kayyali et al. |
| 2003/0068914 A1 | 4/2003 | Merry et al. |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2005/0164551 A1 | 7/2005 | Wlos |
| 2005/0177052 A1 | 8/2005 | Istvan et al. |
| 2005/0203349 A1 | 9/2005 | Nanikashvili |
| 2006/0073728 A1 | 4/2006 | Zaiken et al. |
| 2006/0286861 A1 | 12/2006 | Avevor et al. |
| 2007/0038057 A1 | 2/2007 | Nam et al. |
| 2007/0260133 A1 | 11/2007 | Meyer |
| 2008/0132106 A1 * | 6/2008 | Burnes et al. ............... 439/352 |
| 2009/0099423 A1 | 4/2009 | Al-Ali et al. |

FOREIGN PATENT DOCUMENTS

| | | |
|---|---|---|
| DE | 102 25 621 B3 | 1/2004 |
| DE | 10225621 | 1/2004 |
| DE | 10 2004 032 4 | 1/2006 |
| DE | 102004032410 | 1/2006 |
| EP | 0 766 946 | 4/1997 |
| EP | 0 766 946 A2 | 4/1997 |
| EP | 0 799 628 | 10/1997 |
| EP | 0 799 628 A2 | 10/1997 |
| EP | 1 050 269 | 11/2000 |
| EP | 1 050 269 A1 | 11/2000 |
| EP | 1 932 470 | 6/2008 |
| EP | 1 932 470 A1 | 6/2008 |
| EP | 2 070 474 | 6/2009 |
| EP | 2 070 474 A2 | 6/2009 |
| JP | 2003/010138 | 1/2003 |
| JP | 2004/282608 | 10/2004 |
| WO | WO 03 047 427 | 6/2003 |
| WO | WO 03/047427 A2 | 6/2003 |
| WO | WO 2008/092098 | 7/2008 |
| WO | WO 2008/092098 A2 | 7/2008 |

OTHER PUBLICATIONS

European Search Report corresponding to European Application No. EP 07 25 4691, date of completion is Mar. 25, 2008; 2 pages.
European Search Report corresponding to European Application No. EP 07 25 1765, date of completion is Mar. 31, 2008; 2 pages.
European Search Report corresponding to European Application No. EP 08 16 4409, date of completion is Jan. 27, 2009; 2 pages.
Andreas Boos et al.; "A New Lightweight Fetal Telemetry System"; Dec. 1995; Hewlett-Packard Journal; pp. 82-93.
European Search Report for EP 11 00 6002 dated Nov. 15, 2011.
European Office Action dated Dec. 20, 2011 for European Patent Appln. No. EP 07 253 850.7.
International Search Report corresponding to European Application No. EP 10 01 3624.1; date of completion was Mar. 24, 2011; date of mailing was Apr. 4, 2011; 14 pages.
A&D Company, Limited, "Vital Sensor Graphic Model", No. TM-2560G/TM2564G—TM-2564GP/TM-2564GP, Jan. 1, 2004; pp. 1-62.
A&D Company, Limited, "Vital Sensor Graphic Model", No. TM-2560G/TM2564G-TM-2564GP/TM2564GP, Jan. 1, 2004; pp. 1-62.
International Search Report EP 07 251 765 dated Mar. 31, 2008.
International Search Report EP 07 254 691 dated Mar. 25, 2008.
International Search Report EP 08 164 409 dated Jan. 27, 2009.
European Search Report EP 07 254 691 dated Mar. 25, 2008.
International Search Report corresponding to European Appl. No. EP 10 01 3624.1; date of completion was Mar. 24, 2011; date of mailing was Apr. 4, 2011.
Office Action dated Dec. 11, 2013 for EP Patent Appl. No. 10 013 624.1-1660 which was filed on Oct. 14, 2010, 6pgs.
Office Action dated Nov. 28, 2013 for CN Patent Appl. No. 201010624971.5 which was filed on Oct. 21, 2010, 136pgs.

* cited by examiner

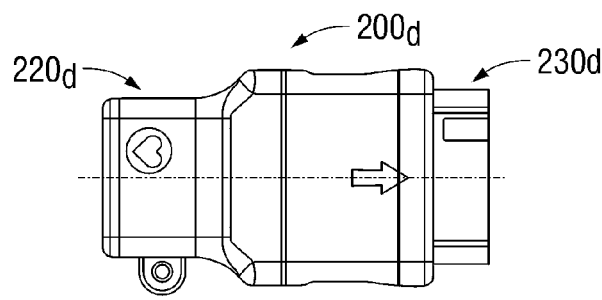
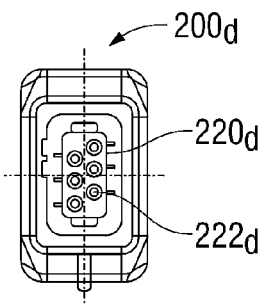
FIG. 18    FIG. 19
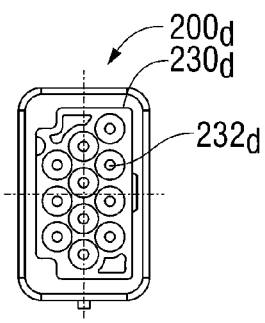
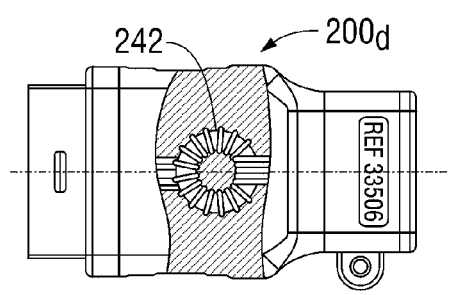
FIG. 20    FIG. 21

ECG LEAD SYSTEM

CROSS-REFERENCE TO RELATED APPLICATION

The present application claims the benefit of and priority to each of U.S. Provisional Application Ser. No. 61/289,144, filed on Dec. 22, 2009, and U.S. Provisional Application Ser. No. 61/253,556, filed on Oct. 21, 2009, the entire content of each of which being incorporated herein by reference.

BACKGROUND

1. Technical Field

The present disclosure relates to medical equipment. In particular, the present disclosure relates to an ECG lead system including an ECG lead set, an adapter system, an extension cable and methods for coupling the ECG lead set with an incompatible ECG device that may monitor or record ECG signals, e.g., an "ECG monitor" or "ECG telemetry."

2. Background of Related Art

Electrocardiograph (ECG) lead systems are widely used to obtain biopotential signals containing information indicative of the electrical activity associated with the heart and pulmonary system. To obtain biopotential signals ECG electrodes are applied to the skin of a patient in various locations and coupled to an ECG device, e.g., an "ECG monitor" or "ECG telemetry." Placement of the electrodes is dependant on the information sought by the clinician.

The placement of the ECG electrodes on the patient has been established by medical protocols. The most common protocols require the placement of the electrodes in a 3-lead, a 5-lead or a 12-lead configuration. A 3-lead configuration requires the placement of three electrodes; one electrode adjacent each clavicle bone on the upper chest and a third electrode adjacent the patient's lower left abdomen. A 5-lead configuration requires the placement of the three electrodes in the 3-lead configuration with the addition of a fourth electrode adjacent the sternum and a fifth electrode on the patient's lower right abdomen. A 12-lead configuration requires the placement of 10 electrodes on the patient's body. Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left arm (Lead I), the right arm and the left leg (Lead II) and the left arm to left leg (Lead III).

Electrodes, after placement on the patient, connect to an ECG device by an ECG lead set. One end of the ECG lead set, closest to the patient, connects to each electrode (alternatively, the electrodes may be integrated into the distal end of the ECG lead set) and receives biopotential signals from the body. The other end of the ECG lead set connects to the ECG input connector and supplies the biopotential signals received from the body to the ECG device.

ECG devices and ECG lead sets are manufactured and sold by various companies. Although protocols have been established for the placement ECG electrodes, the various manufacturers typically use product specific connectors and wiring configurations.

Problems occur when an ECG lead set and an ECG monitor are electrically incompatible but have mechanically compatible connectors. While some problems may be automatically detected by the ECG device, other problems, such as, for example, the incorrect order of V1-V6, may go undetected and the ECG device may provide the clinician with erroneous information.

Some ECG devices are configured to connect to a specific type or family of ECG lead sets manufactured, distributed and sold by the same manufacturer of the ECG device. The ECG device, and specific type or family of ECG lead sets, may utilize, as a safety feature, a unique or specialized connector that is only compatible with the particular ECG device and incompatible with all other ECG lead sets.

While this safety feature may prevent a clinician from accidentally connecting an incompatible lead set to an ECG device, it also requires each medical facility to supply a plurality of ECG lead sets for the various ECG device used within a medical facility.

Additionally, in many instances, a patient may require one type of ECG lead system while in, for example, the emergency room (ER), the operating room (OR), the post-anesthesia care unit (PACU), the intensive care unit (ICU) and/or the critical care unit (CCU); and may require a second or different type ECG lead system while on, for example, a telemetry floor. In particular, a patient may require a relatively longer ECG lead set in order to connect to an ECG monitor while the patient is in the ER, the OR, the PACU, the ICU and/or the CCU; and a relatively shorter ECG lead set in order to connect to an ECG telemetry while the patient is on a telemetry floor.

Accordingly, a need exists for a system that will enable an end user to use a single ECG lead set across various ECG device platforms and to accommodate the use of the ECG lead set with either an ECG monitor and/or ECG telemetry as needed and7/or desired.

The present application provides an ECG lead set, adapter system and methods for coupling a standard ECG lead set with any incompatible ECG device thus preventing the aforementioned concerns.

SUMMARY

The present disclosure relates to an ECG lead system including an ECG lead set, an adapter system, an extension cable and methods for coupling the ECG lead set with an incompatible ECG device that may monitor or record ECG signals, e.g., an "ECG monitor" or "ECG telemetry."

According to an aspect of the present disclosure, an ECG lead system for use with an ECG floor monitor for when a patient is substantially immobile and/or an ECG telemetry monitor is provided. The ECG lead system includes an ECG lead set assembly, including an ECG lead set cable having a length; a plurality of electrode connectors disposed at a first end of the ECG lead set cable, wherein the electrode connectors are configured to electrically connect to electrodes placed on a patient; and a device connector disposed at a second end of the ECG lead set cable. The ECG lead system further includes an ECG lead extension assembly, including an ECG lead extension cable having a length greater that the length of the ECG lead set cable; an ECG lead set assembly connector disposed at a first end of the ECG lead extension cable, wherein the ECG lead set assembly connector is configured and adapted to mate with and electrically connect to the device connector of the ECG lead set assembly; and a device connector disposed at a second end of the ECG lead extension cable. In use, when the patient is connected to the ECG floor monitor, the ECG lead extension assembly is connected between the ECG lead set assembly and the ECG floor monitor; and when the patient is connected to the ECG telemetry monitor, the ECG lead set assembly is directly connected to the ECG telemetry monitor.

Each electrode connector may include a housing defining an aperture therein; a lead wire terminal disposed within the housing and accessible through the aperture of the housing, wherein the lead wire terminals are electrically connectable to the electrodes placed on the patient; a contact plate electrically connected to the lead wire terminal, the contact plate defines a keyhole slot that is in registration with the aperture of the housing, the keyhole slot includes a first slot portion and a second slot portion, wherein the first slot portion has an internal diameter which is greater than an internal diameter of the second slot portion; and a lever pivotably connected to the housing and is biased to a first position, wherein the lever includes a cam finger projecting therefrom so as to extend across the first slot portion of the keyhole slot when the lever is in the first position.

The lever may be actuatable to a second position wherein the cam finger does not extend across the first slot portion of the keyhole slot.

Each electrode connector may include a biasing member disposed within the housing and operatively engaged with the lever to bias the lever to the first position.

The ECG lead system may further include a latching system for increasing a disconnection force required to disconnect the device connector of the ECG lead set cable and the ECG lead set assembly connector of the ECG lead extension assembly.

The latching system may include a locking tab insertable into a recess of the device connector of the ECG lead set cable and a recess of the ECG lead set assembly connector of the ECG lead extension assembly, wherein the recesses are in registration with one another when the device connector of the ECG lead set cable and the ECG lead set assembly connector of the ECG lead extension assembly are connected to one another.

The latching system may include a latch arm pivotably connected to the device connector of the ECG lead set cable, wherein the latch arm is pivotable to a closed position wherein a tab extending therefrom is inserted into a recess defined in a surface of the ECG lead set assembly connector of the ECG lead extension assembly.

The latching system may include a pair of resilient flaps extending distally from opposed side edges of the device connector of the ECG lead set cable, wherein pair of resilient flaps project toward one another, and wherein the pair of flaps overlie a surface of the ECG lead set assembly connector of the ECG lead extension assembly when the ECG lead set assembly connector is connected to the device connector of the ECG lead set cable.

The ECG lead system may further include a plurality of unique adapters, wherein each adapter includes an input receptacle configured for selective electrical connection with the device connector of the ECG lead set assembly; and at least one unique monitor plug electrically connected to the input receptacle, wherein each monitor plug is configured to selectively electrically connect to a corresponding receptacle of a respective unique ECG floor monitor or ECG telemetry monitor.

The unique monitor plug of the adapter may have a configuration selected from the group consisting of an AAMI type (6 pin) configuration, a GE/Marquette type (11 pin) configuration, a Philips type (12 pin) configuration, a HP type (8 pin) configuration, a Spacelabs type (17 pin) configuration, a D-Subminiature type (15 pin) configuration, a D-Subminiature HP Pagewriter type (15 pin) configuration, a Datex type (10 Pin) configuration, a Medtronic type (12 pin) configuration, and a Spacelabs Dual Connect type (5 pin) configuration.

According to another aspect of the present disclosure, an ECG lead system for use with a plurality of unique diverse ECG floor monitors for when a patient is substantially immobile and/or a plurality of unique diverse ECG telemetry monitors is provided. The ECG lead system includes a plurality of unique adapters, wherein each adapter includes an input receptacle configured for selective electrical connection with a device connector of an ECG lead set assembly; and at least one unique monitor plug electrically connected to the input receptacle, wherein each monitor plug is configured to selectively electrically connect to a corresponding receptacle of a respective unique diverse ECG floor monitor or unique diverse ECG telemetry monitor.

The unique monitor plug of the adapter may have a configuration selected from the group consisting of an AAMI type (6 pin) configuration, a GE/Marquette type (11 pin) configuration, a Philips type (12 pin) configuration, a HP type (8 pin) configuration, a Spacelabs type (17 pin) configuration, a D-Subminiature type (15 pin) configuration, a D-Subminiature HP Pagewriter type (15 pin) configuration, a Datex type (10 Pin) configuration, a Medtronic type (12 pin) configuration, and a Spacelabs Dual Connect type (5 pin) configuration.

The ECG lead system may further have an ECG lead set assembly, including an ECG lead set cable having a length; a plurality of electrode connectors disposed at a first end of the ECG lead set cable, wherein the electrode connectors are configured to electrically connect to electrodes placed on a patient; and a device connector disposed at a second end of the ECG lead set cable, wherein the device connector is configured for selective electrical connection with the input receptacle of the adapter.

Each adapter may include a polarizing element, and wherein the device connector may include a complementary polarizing element to mating with the polarizing element of each adapter when a selected adapter is connected to the device connector.

The ECG lead system may further have an ECG lead extension assembly, including an ECG lead extension cable having a length greater that the length of the ECG lead set cable; an ECG lead set assembly connector disposed at a first end of the ECG lead extension cable, wherein the ECG lead set assembly connector is configured and adapted to mate with and electrically connect to the device connector of the ECG lead set assembly; and a device connector disposed at a second end of the ECG lead extension cable. In use, when the patient is connected to a unique diverse ECG floor monitor, the ECG lead extension assembly may be connected between the ECG lead set assembly and the unique diverse ECG floor monitor, via a corresponding adapter; and when the patient is connected to a unique diverse ECG telemetry monitor, the ECG lead set assembly may be connected to the unique diverse ECG telemetry monitor, via a corresponding adapter.

According to a further aspect of the present disclosure, a method of connecting a patient to any of a plurality of unique diverse ECG floor monitors for when a patient is substantially immobile and/or a plurality of unique diverse ECG telemetry monitors is provided. The method includes the steps of providing an ECG lead system, the ECG lead system including a plurality of unique adapters, wherein each adapter includes an input receptacle configured for selective electrical connection with a device connector of an ECG lead set assembly; and at least one unique monitor plug electrically connected to the input receptacle, wherein each monitor plug is configured to selectively electrically connect to a corresponding receptacle of a respective unique diverse ECG floor monitor or unique diverse ECG telemetry monitor. The ECG lead system further includes an ECG lead set assembly, including an ECG lead set cable having a length; a plurality of electrode connectors disposed at a first end of the ECG lead set cable, wherein the electrode connectors are configured to electrically connect to electrodes placed on a patient; and a device connector disposed at a second end of the ECG lead set cable, wherein the device connector is configured for selective electrical connection with the input receptacle of the adapter.

The method further includes the steps of determining the type of ECG floor monitor or ECG telemetry monitor to be used; selecting an adapter from the plurality of unique adapters that corresponds to the type of ECG floor monitor or ECG telemetry monitor to be used; and connecting the device connector of the ECG lead set assembly to the ECG floor monitor or ECG telemetry monitor that is being used via the selected adapter.

According to a further aspect of the present disclosure, an ECG lead system for use with an ECG monitoring system is provided. The ECG lead system comprises a lead set assembly, including a lead cable; a plurality of electrode connectors disposed along a first end of the lead cable configured to electrically connect to a plurality of electrodes disposed on a patient, and a device connector disposed along a second end of the lead cable. Each electrode connector includes a housing; and a lever connected to the housing, the lever having a first position to enable connection of an electrode to the electrode connector and a second position to inhibit disconnection of the electrode from the electrode connector. The ECG lead system further comprises a lead adaptor that electrically couples the lead set assembly to the ECG monitoring system, including an adapter body; an input receptacle disposed along a first end of the adaptor body, wherein the input receptacle is configured to electrically connect to the device connector of the lead set assembly; and an output receptacle disposed along a second end of the adaptor body, wherein the output receptacle is configured to electronically connect to the ECG monitoring system.

The device connector may be operably coupled to at least one of the ECG floor monitor and a ECG telemetry monitor.

The ECG lead system may further include an extension cable interconnecting the lead cable and the lead adapter. The extension cable may include a lead set assembly connector disposed at a first end thereof, wherein the lead set assembly connector is configured to mate with and electronically connect to the device connector of the lead set assembly. The extension cable may include a lead adapter connector disposed at a second end of the thereof, wherein the lead adapter connector is configured to mate with and electronically connect to the input receptacle of the lead adapter.

The input receptacle of the lead adaptor may be one of a single and a pair of input receptacles. The output receptacle of the lead adaptor may be selected from the group consisting of a AAMI type (6 pin) plug, a GE/Marquette type (11 pin) plug, a Philips type (12 pin) plug, a HP type (8 pin) plug, a Spacelabs type (17 pin) plug, a D-Subminiature type (15 pin) plug, a D-Subminiature HP Pagewriter type (15 pin) plug, a DATEX type (10 pin) plug, and a MEDTRONIC type (12 pin) plug.

According to yet another aspect of the present disclosure, a method of monitoring ECG data is provided. The method includes the steps of providing a lead set assembly having a cable including a plurality of electrode connectors, said electrode connectors having a housing and a lever connected to the housing; providing a plurality of diverse lead adaptors; electrically connecting a selected one of the plurality of diverse lead adaptors corresponding to a ECG monitoring system to be used; electrically connecting the lead set assembly to the selected one of the plurality of diverse lead adaptors; placing a plurality of electrodes on a patient; and electrically connecting and securing the plurality of electrode connectors of the lead set assembly to specific electrodes placed on the patient by actuation of said lever from the first position to the second position inhibiting disconnection of the electrode.

According to another aspect of the present disclosure, a ECG lead kit for monitoring ECG data is provided. The kit includes a lead set assembly, having a lead cable; and a plurality of electrode connectors disposed along a first end of the lead cable configured to electrically connect to a plurality of electrodes disposed on a patient. Each electrode connector includes a housing; and a lever connected to the housing, the lever having a first position to enable connection of an electrode to the electrode connector and a second position to inhibit disconnection of the electrode from the electrode connector, wherein actuation of said lever from the first position to the second position inhibits disconnection of the electrode. The lead assembly also includes a device connector disposed along a second end of the lead cable.

The kit also includes a lead adaptor that electrically couples the lead set assembly to the ECG monitoring system, including an adapter body; an input receptacle disposed along a first end of the adaptor body, wherein the input receptacle is configured to electrically connect to the device connector of the lead set assembly; and an output receptacle disposed along a second end of the adaptor body, wherein the output receptacle is configured to electronically connect to the ECG monitoring system.

The kit further includes an extension cable interconnecting the lead cable and the lead adapter. The extension cable includes a lead set assembly connector disposed at a first end thereof, wherein the lead set assembly connector is configured to mate with and electronically connect to the device connector of the lead set assembly; and a lead adapter connector disposed at a second end of the thereof, wherein the lead adapter connector is configured to mate with and electronically connect to the input receptacle of the lead adapter.

The input receptacle of the lead adaptor may be one of a single and a pair of input receptacles. The output receptacle of the lead adaptor may be selected from the group consisting of a AAMI type (6 pin) plug, a GE/Marquette type (11 pin) plug, a Philips type (12 pin) plug, a HP type (8 pin) plug, a Spacelabs type (17 pin) plug, a D-Subminiature type (15 pin) plug, a D-Subminiature HP Pagewriter type (15 pin) plug, a DATEX type (10 pin) plug, and a MEDTRONIC type (12 pin) plug.

DETAILED DESCRIPTION OF THE DRAWINGS

Various embodiments of the present disclosure are described herein with reference to the drawings wherein:

FIGS. 18-21 illustrate still another particular embodiment of the adapter of FIGS. 8-10;

FIGS. 50A-50e illustrate a latching system, according to another embodiment of the present disclosure, for use with the ECG lead system of the present disclosure;

DETAILED DESCRIPTION OF EMBODIMENTS

Particular embodiments of the present disclosure are described hereinbelow with reference to the accompanying drawings. In the following description, well-known functions or constructions are not described in detail to avoid obscuring the present disclosure in unnecessary detail. As used herein and as is traditional, the term "distal" refers to the portion which is furthest from the user/clinician and the term "proximal" refers to the portion that is closest to the user/clinician. In addition, terms such as "above", "below", "forward", "rearward", etc. refer to the orientation of the figures or the direction of components and are simply used for convenience of description.

Figure 1:
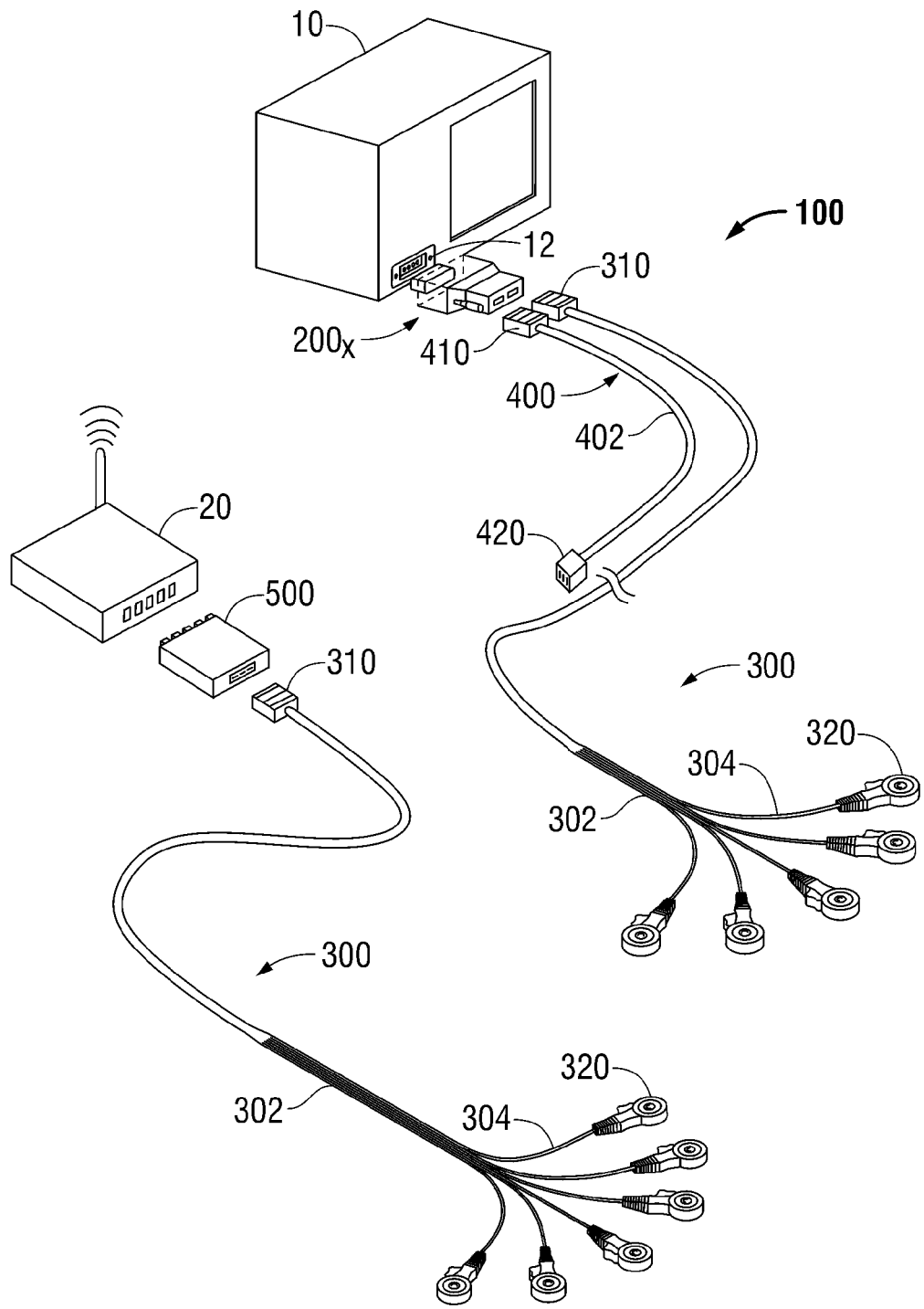
FIG. 1 is a schematic of an ECG lead system according to the present disclosure, incorporating an ECG adapter system and ECG lead set assemblies.
Figure 48:
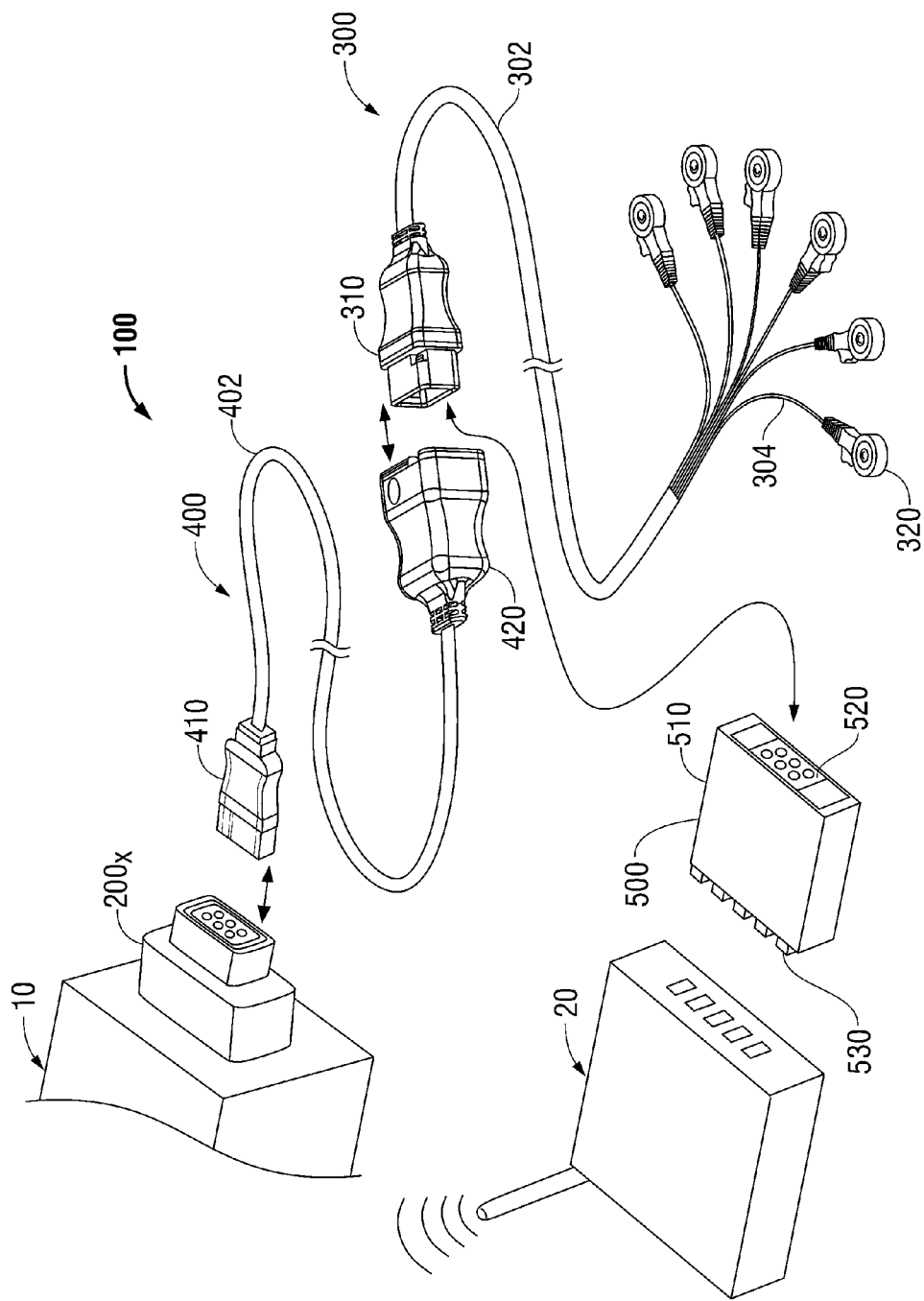
FIG. 48 is a schematic illustration of the ECG lead system according to the present disclosure, incorporating an ECG adapter system, an ECG lead set assembly and an ECG lead extension assembly, for connection to an ECG monitor and/or ECG telemetry.

As seen in FIGS. 1 and 48, an ECG lead system 100, in accordance with the present disclosure, is used in connection with an ECG device or monitor, in the form or an ECG floor monitor 10 or ECG telemetry monitor 20. ECG floor monitor 10 includes at least one lead set input connector 12 configured to connect with at least one compatible ECG lead set assembly. ECG lead system 100 includes any one of a number of adapters $200_X$, depending on the type of ECG floor monitor 10 or ECG telemetry monitor 20 present, on whether a 3-lead, a 5-lead or a 12-lead electrode set assembly 300 is used, and on whether one or more ECG lead set assemblies 300 are used.

Figure 2:
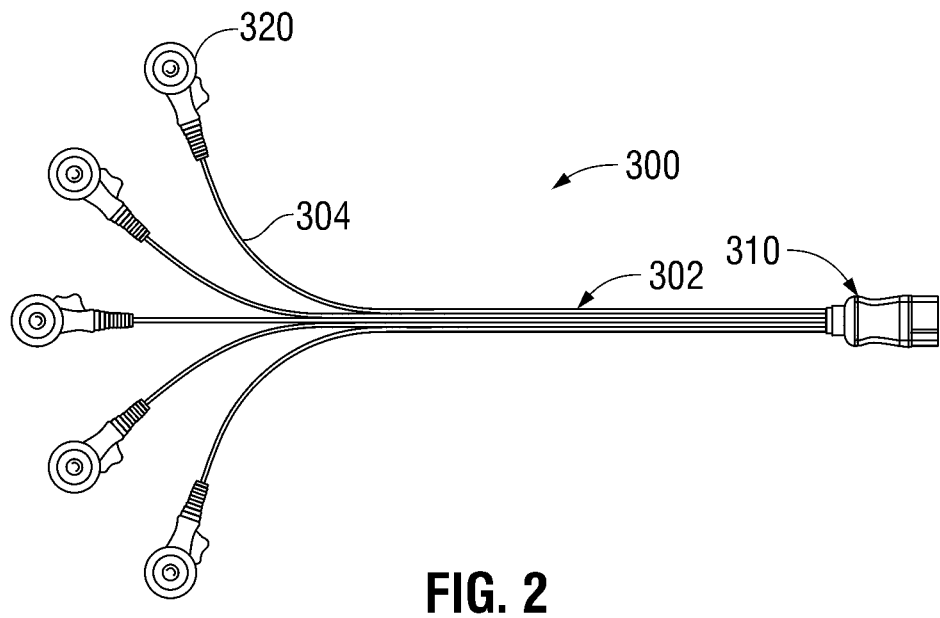
FIG. 2 is a plan view of an ECG lead set assembly of the ECG lead system of FIG. 1.

As seen in FIG. 2, each ECG lead set assembly 300 includes a lead set cable 302, a device connector 310 at one end of the lead set cable 302 and a plurality of electrode connectors 320 some of which are at the other end of the lead set cable 302. Lead set cable 302 includes a plurality of encased and insulated lead wires 304 disposed in side by side relation. Insulated lead wires 304 may be EMI/RF shielded. Lead set cable 302 is in the form of a ribbon cable configured for transmitting electrical signals.

Each lead wire 304 is independently separable from an adjacent lead wire 304 to facilitate placement of a respective electrode connector 320 at a predetermined body location, to thereby permit customization of the ECG lead set assembly 300 for each subject. Lead wires 304 are attached via their insulated covers and, are separable along respective lines of juncture of the insulated covers of adjacent lead wires 304. Individual lead wires 304 of lead set cable 302 may be varied in length to permit placement of an individual electrode connector 320 at a target site, e.g. across the chest or abdomen, to permit collection or delivery of biomedical signals at these locations.

Figure 3:
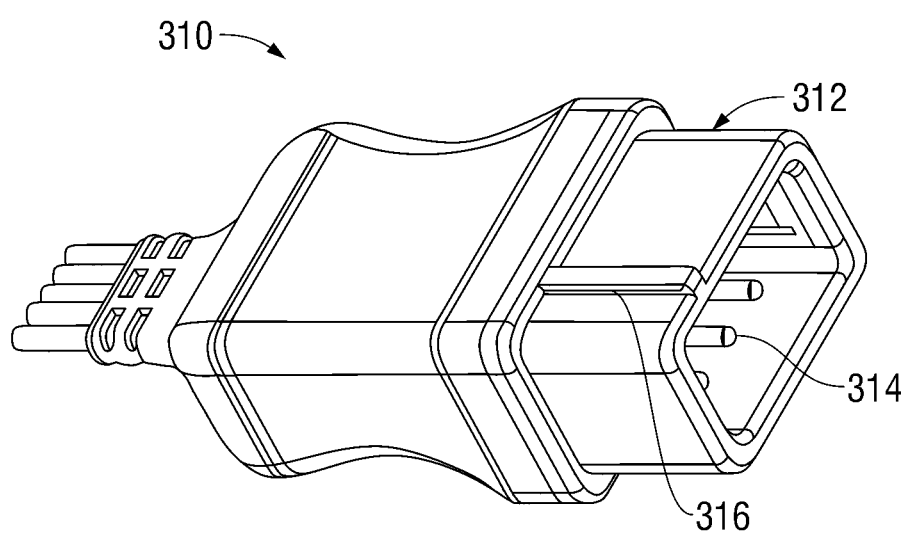
FIG. 3 is an enlarged perspective view of a device connector of the ECG lead set assembly of FIG. 2.

As seen in FIGS. 2 and 3, device connector 310 is a six (6) pin male connector or a ten (10) pin male connector, similar to D-subminiature connectors, e.g., those used for computers and other electronic equipment.

Figure 4:
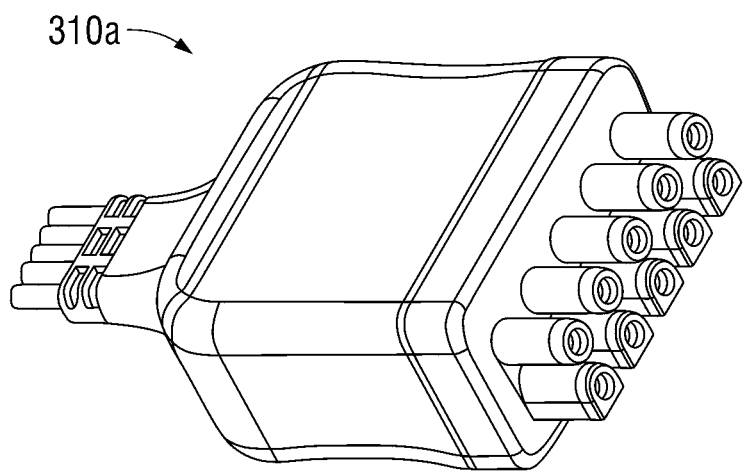
FIG. 4 is an enlarged perspective view of an alternate device connector of the ECG lead set assembly of FIG. 2.

As seen in FIG. 4, device connector 310a is a five (5) plug (for 5 leads, wherein each plug transmits an ECG signal across a socket and shield signal across the other socket), ten (10) pin male socket connector, similar to those used for GE/Marqutte leadwire to trunk cable interconnections.

Figure 5:
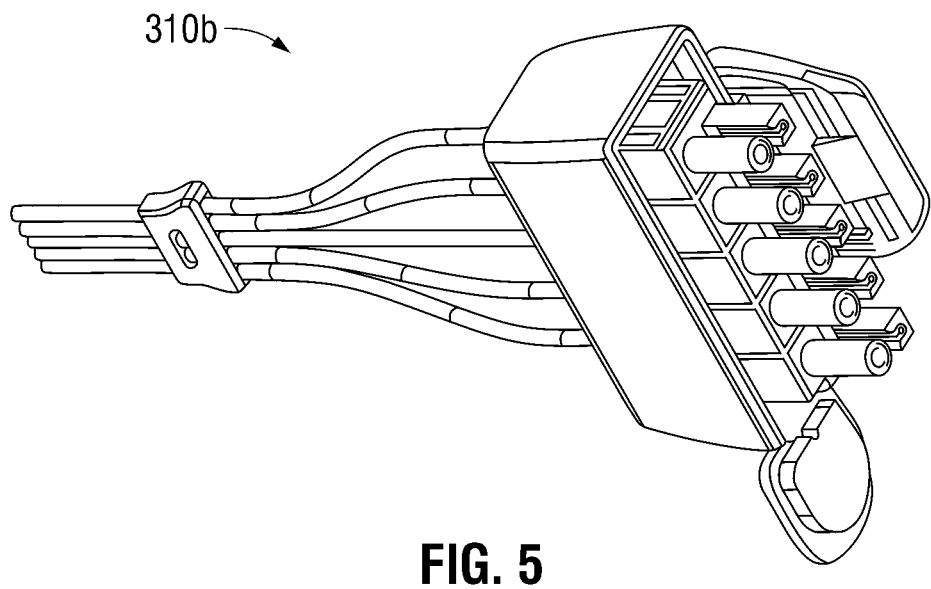
FIG. 5 is an enlarged perspective view of yet another device connector of the ECG lead set assembly of FIG. 2.

As seen in FIG. 5, device connector 310b is a five (5) plug (each plug having a pair of sockets, wherein one plug corresponds to one ECG lead and the corresponding plug carries the shield), ten (10) pin male socket connector, similar to those specified by ANSI/AAMI EC53 for shielded leadwire to trunk cable interconnections. Device connector 310b includes a locking member 312 configured and dimensioned to engage a complimentary locking feature of a telemetry unit or the like (not shown).

Device connector 310 of FIGS. 2 and 3 is coupled to the proximal end of lead set cable 302 and is configured to couple with any one of a number of lead set adapters $200_X$. Device connector 310 of lead set assembly 300 is not configured for direct connection (mechanically and/or physically incompatible) to the lead set input connector 12 of the ECG floor monitor 10 or ECG telemetry monitor 20.

As seen in FIG. 3, device connector 310 includes a longitudinally extending perimeteral wall 312 bounding the male connector pins 314 and defining a longitudinally extending rib 316 projecting from an outer surface of perimeteral wall 312. Rib 316 functions as a polarizing element for ensuring proper connection of device connector 310 to any one of a number of adapters $200_X$.

Figure 6:
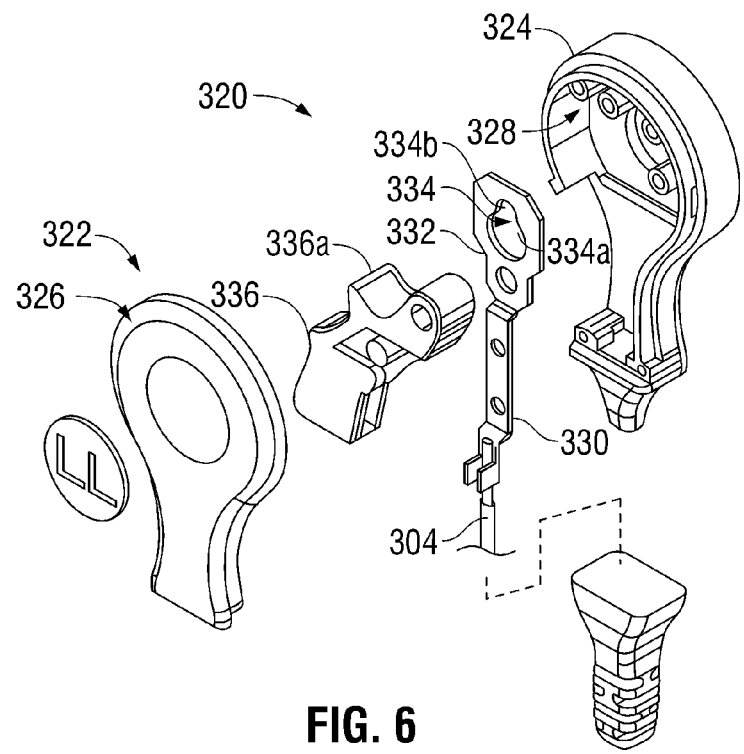
FIG. 6 is a perspective view, with parts separated, of an electrode connector of the ECG lead set assembly of FIG. 2.
Figure 7:
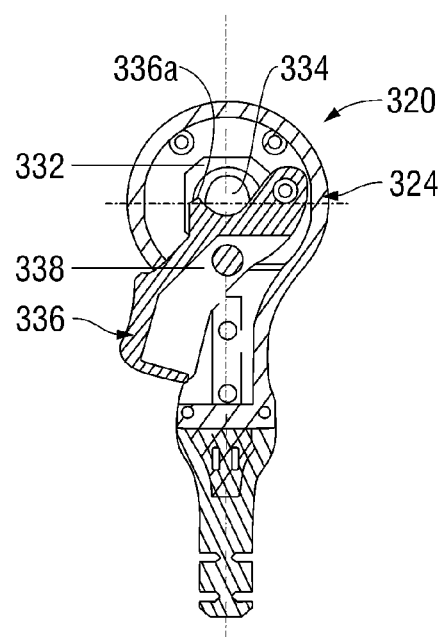
FIG. 7 is a cross-sectional view of electrode connector of FIG. 6.

As seen in FIGS. 1 and 2, a distal end of each lead wire 304 is connected to an electrode connector 320. Electrode connectors 320 are configured to connect to an ECG electrode (not shown) that is placed on a patient. As seen in FIGS. 6 and 7, each electrode connector 320 includes a housing 322 having an upper member 324 and a lower member 326, and defining an internal cavity 328 therebetween. Housing 322 is fabricated from a non-conducting material, e.g., an injection molded polymer which electrically insulates the subject from the conductive element(s) therewithin. Upper member 324 and lower member 326 are separate components attached to each other by conventional means and form a non-conductive element of the housing 322.

Housing 322 includes a lead wire terminal 330 which is electrically connected to a respective end of lead wire 304. Housing 322 supports a contact plate 332 that is electrically connected to lead wire terminal 330. Contact plate 332 defines a keyhole slot 334 formed therein and in communication with internal cavity 328 of housing 322. Keyhole slot 334 includes first slot portion 334a and second slot portion 334b. First slot portion 334a defines an internal dimension or diameter which is greater than the corresponding internal dimension or diameter of second slot portion 334b.

Housing 322 further includes a lever 336 pivotably connected thereto. Lever 336 is biased to a first position by a biasing member 338. Lever 336 includes a cam finger 336a projecting therefrom so as to extend across first slot portion 334a of keyhole slot 334 when lever 336 is in the first position. In use, lever 336 is actuatable to a second position wherein cam finger 336a thereof does not obstruct or extend across first slot portion 334a of keyhole slot 334.

Electrode connector 320 is adapted for connection to a conventional snap-type biomedical electrode (not shown). A typical snap-type biomedical electrode incorporates an electrode flange or base and male stud or terminal extending in transverse relation to the electrode base. The male terminal may have a bulbous head whereby an upper portion of the male terminal has a greater cross-sectional dimension than a lower portion of the male terminal. Accordingly, in use, when lever 336 of electrode connector 320 is in the second position, the head of the male terminal of the snap-type biomedical electrode may be inserted into first slot portion 334a of keyhole slot 334 and lever 336 may be released so that biasing member 338 moves cam finger 336a of lever 336 against the head of the male terminal to push or force the lower portion of the male terminal into second slot portion 334b of keyhole slot 334. The biasing force of biasing member 338 helps to maintain the male terminal within second slot portion 334b of keyhole slot 334 and thus inhibits removal or disconnection of the biomedical electrode from connector 320.

ECG lead set assembly 300 may have a length of approximately 3.0' (1.0 m).

Figure 8:
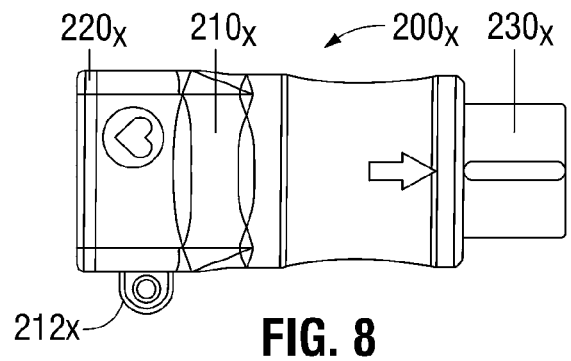
FIG. 8 is a top plan view of an adapter of the ECG lead system of FIG. 1.
Figure 9:
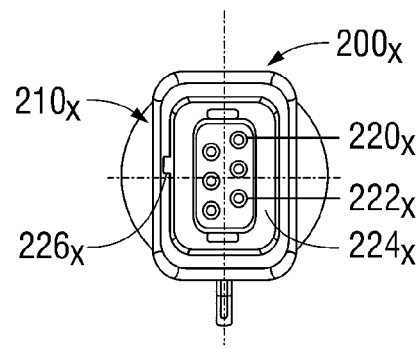
FIG. 9 is a front elevational view of the adapter of FIG. 8.
Figure 10:
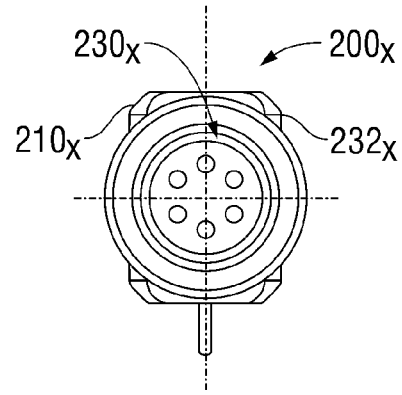
FIG. 10 is a rear elevational view of the adapter of FIG. 8.

Turning now to FIGS. 8-41, ECG lead system 100 includes a plurality of adapters $200_X$ for use with ECG lead set assembly 300. Each adapter $200_X$ electrically couples the ECG lead set assembly 300 to the ECG floor monitor 10 or the ECG telemetry monitor 20. As seen in FIGS. 8-10, each adapter $200_X$ generally includes an adapter body $210_X$, at least one input receptacle $220_X$ disposed on one side of adapter body $210_X$, and a monitor plug $230_X$ disposed on another side of adapter body $210_X$. Each input receptacle $220_X$ is configured to electrically couple with a device connector 310.

Each input receptacle $220_X$ includes a plurality of electrical contact receptacles $222_X$ for connection with the male pin contacts 314 of the device connector 310 (FIGS. 1 and 2) of lead set assembly 300. Each input receptacle $220_X$ includes an annular channel $224_X$ surrounding the contact receptacles $222_X$ and being configured to receive perimeteral wall 312 of device connector 310. Each input receptacle $220_X$ includes a longitudinally extending slot or channel $226_X$ for mating with longitudinally extending rib 316 of perimeteral wall 312 of device connector 310. In this manner, device connector 310 may be connected to adapter $200_X$ in only one orientation.

Monitor plug $230_X$ is configured for coupling to the lead set input connector 12 of the ECG floor monitor 10. Monitor plug $230_X$ includes a plurality of male contact pins $232_X$ for establishing an electrical connection between the ECG floor monitor 10 and the contact receptacles $222_X$ of input receptacle $220_X$.

Figure 11:
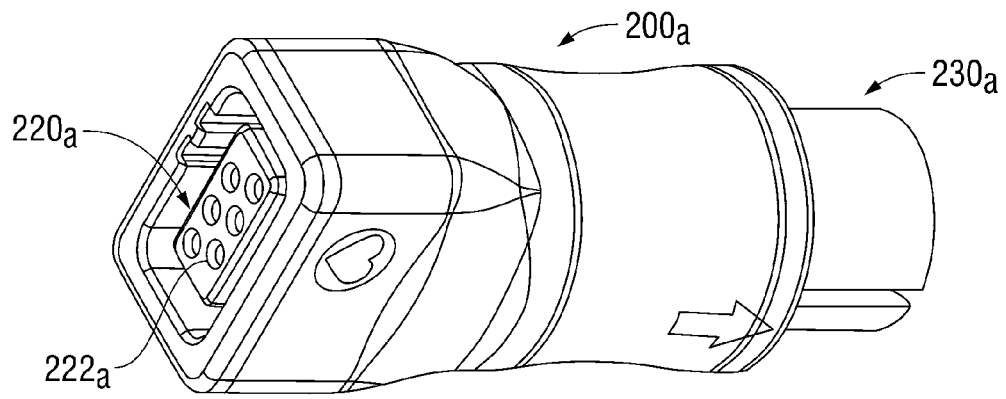
FIGS. 11 and 12 illustrate a particular embodiment of the adapter of FIGS. 8-10.
Figure 12:
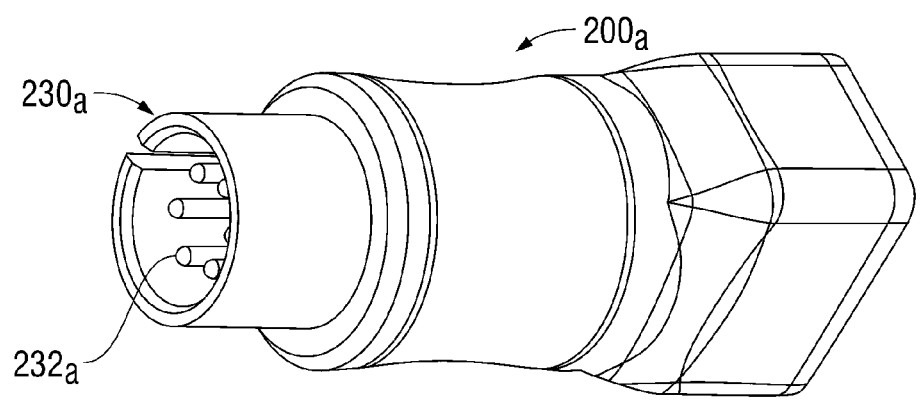

As seen in FIGS. 11 and 12, in one embodiment, adapter $200_a$ includes a single input receptacle $220_a$, and an AAMI type (6 pin) monitor plug $230_a$. Adapter $200_a$ may include a resistor element electrically interposed between at least one contact receptacle $222_a$ of input receptacle $220_a$ and at least one male contact pin $232_a$ of monitor plug $230_a$. In this embodiment, not all of the male contact pins $232_a$ of monitor plug $230_a$ need to be connected to the contact receptacles $222_a$ of input receptacle $220_a$.

Figure 13:
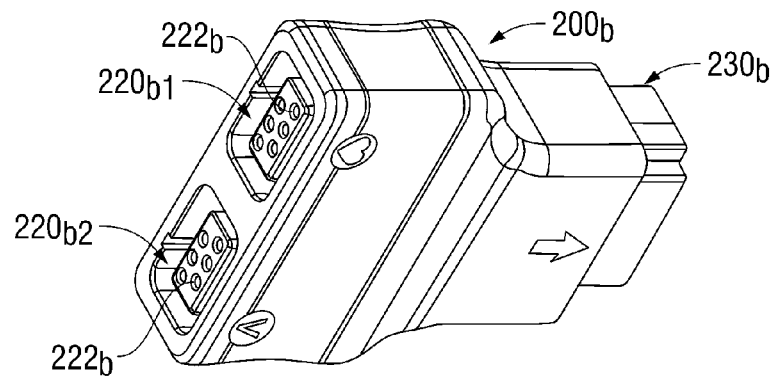
FIGS. 13-15 illustrate another particular embodiment of the adapter of FIGS. 8-10.
Figure 14:
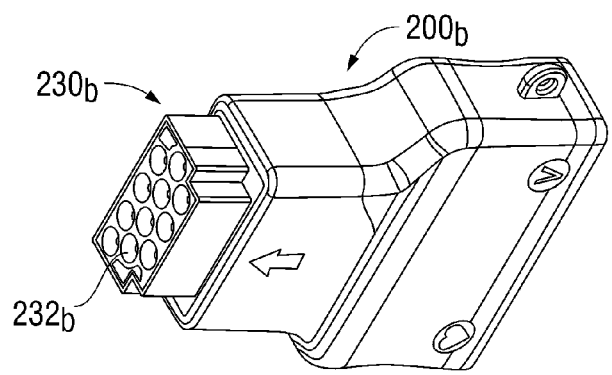
Figure 15:
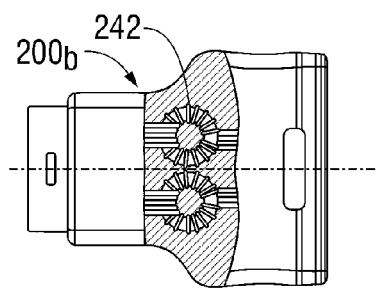

As seen in FIGS. 13-15, in an embodiment, adapter $200_b$ includes a pair of input receptacles $220_{b1,b2}$, and a GE/Marquette type (11 pin) monitor plug $230_b$. Adapter $200_b$ includes an inductor element 242 electrically interposed between contact receptacles $222_b$ of each input receptacle $220_{b1,b2}$ and the male contact pins $232_b$ of monitor plug $230_b$. In this embodiment, all of the male contact pins $232_b$ of monitor plug $230_b$ are connected to a contact receptacle 224 of input receptacles $220_{b1,b2}$.

Figure 16:
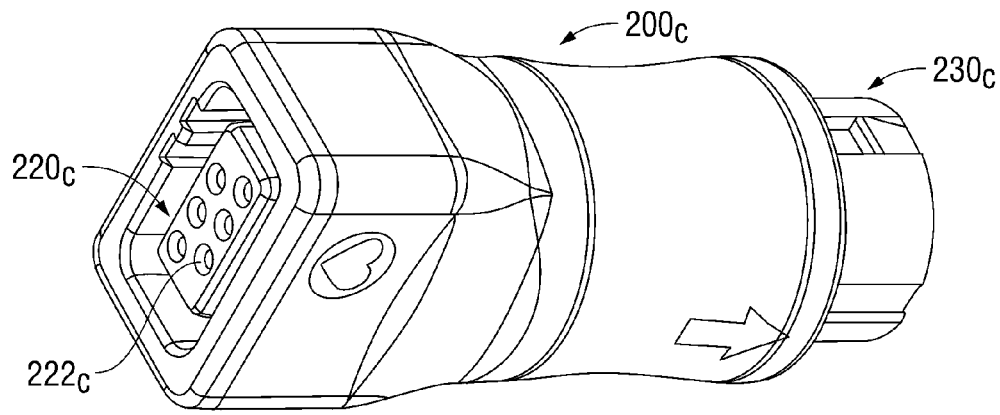
FIGS. 16 and 17 illustrate yet another particular embodiment of the adapter of FIGS. 8-10.
Figure 17:
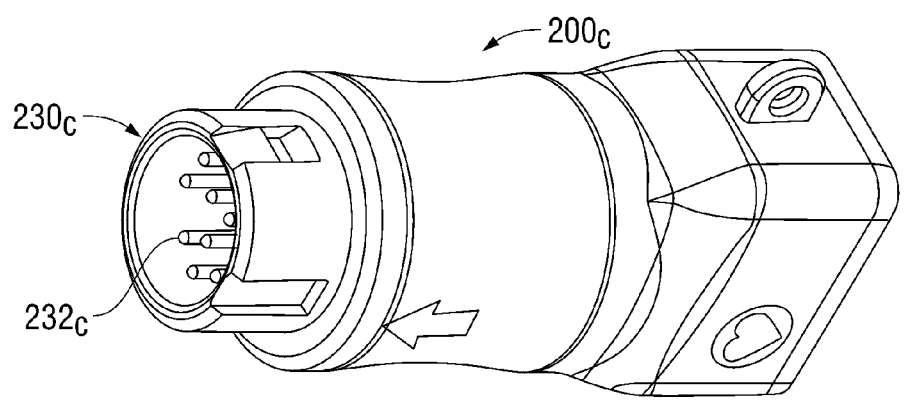

As seen in FIGS. 16 and 17, in another embodiment, adapter $200_c$ includes a single input receptacle $220_c$ and a Philips type (12 pin) monitor plug $230_c$. Adapter $200_c$ may include a resistor element electrically interposed between contact receptacles $222_c$ of input receptacle $220_c$ and the male contact pins $232_c$ of monitor plug $230_c$. In this embodiment, not all of the male contact pins $232_c$ of monitor plug $230_c$ are connected to contact receptacles $222_c$ of input receptacle $220_c$.

As seen in FIGS. 18-21, in yet another embodiment, adapter $200_d$ includes a single input receptacle $220_d$, and a GE/Marqutte type (11 pin) monitor plug $230_d$. Adapter $200_d$ includes an inductor element 242 electrically interposed between contact receptacles $222_d$ of input receptacle $220_d$ and the male contact pins $232_d$ of monitor plug $230_d$. In this embodiment, not all of the male contact pins $232_d$ of monitor plug $230_d$ are connected to contact receptacles $222_d$ of input receptacle $220_d$.

Figure 22:
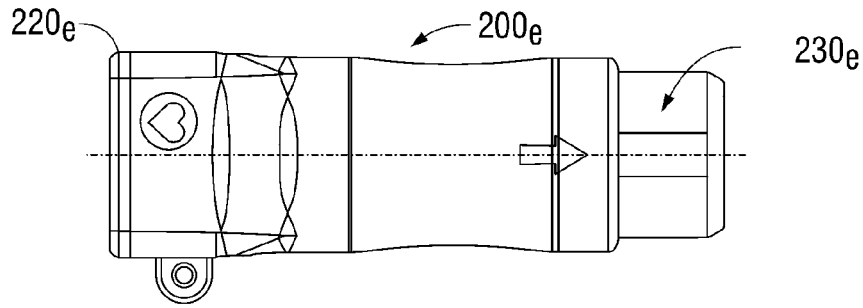
FIGS. 22-24 illustrate a further particular embodiment of the adapter of FIGS. 8-10.
Figure 23:
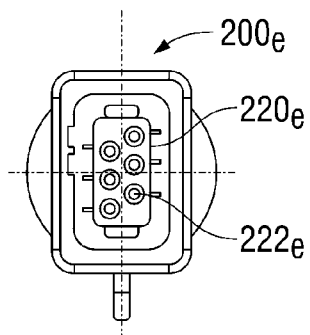
Figure 24:
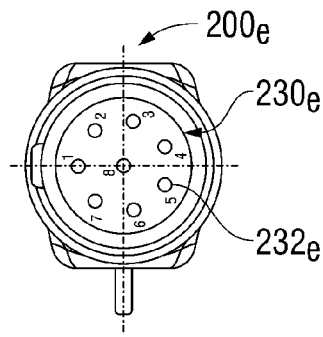

As seen in FIGS. 22-24, in still another embodiment, adapter $200_e$ includes a single input receptacle $220_e$, and a HP type (8 pin) monitor plug $230_e$. Adapter $200_e$ may include a resistor element electrically interposed between contact receptacles $222_e$ of input receptacle $220_e$ and the male contact pins $232_e$ of monitor plug $230_e$. In this embodiment, not all of the male contact pins $232_e$ of monitor plug $230_e$ are connected to contact receptacles $222_e$ of input receptacle $220_e$.

Figure 25:
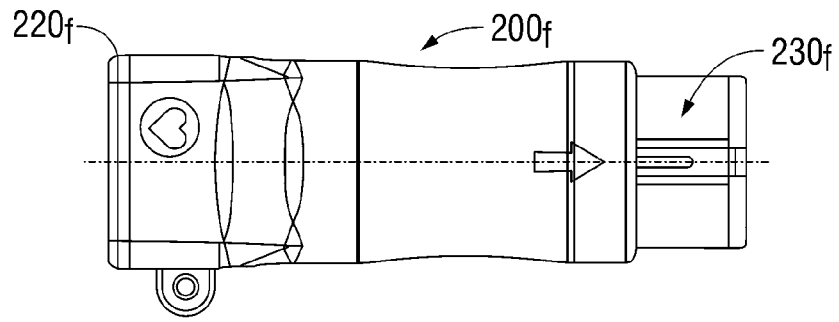
FIGS. 25-27 illustrate still a further particular embodiment of the adapter of FIGS. 8-10.
Figure 26:
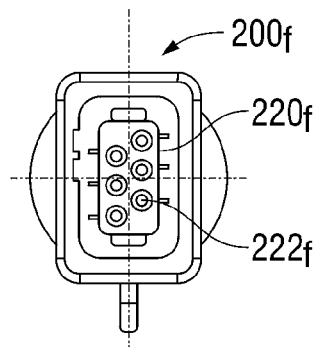
Figure 27:
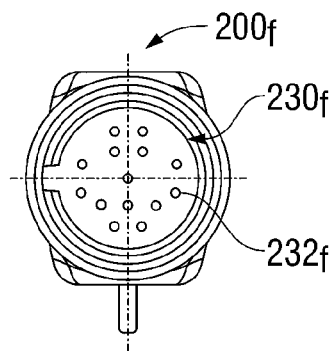

As seen in FIGS. 25-27, in an embodiment, adapter $200_f$ includes a single input receptacle $220_f$, and a Spacelabs type (17 pin) monitor plug $230_f$. Adapter $200_f$ may include a resistor element electrically interposed between contact receptacles $222_f$ of input receptacle $220_f$ and the male contact pins $232_f$ of monitor plug $230_f$. In this embodiment, not all of the male contact pins $232_f$ of monitor plug $230_f$ are connected to contact receptacles $222_f$ of input receptacle $220_f$.

Figure 28:
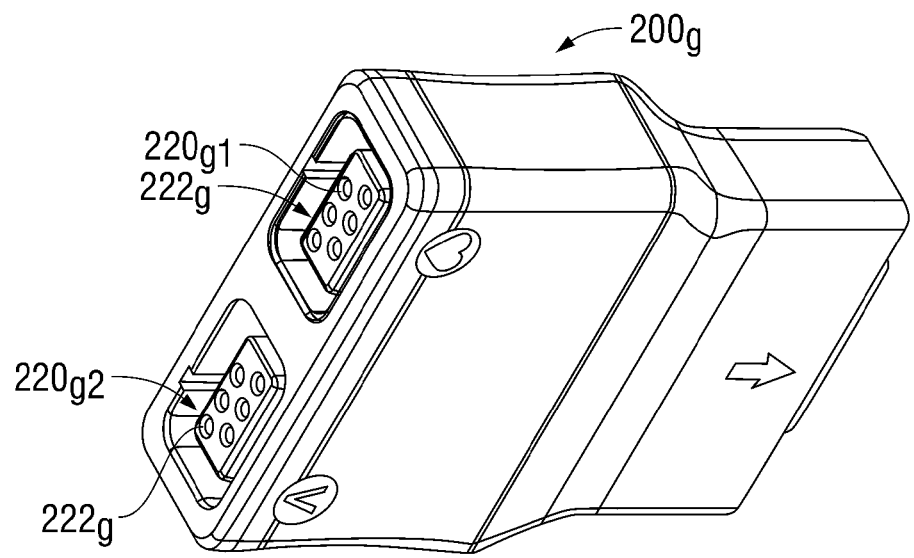
FIGS. 28 and 29 illustrate another particular embodiment of the adapter of FIGS. 8-10.
Figure 29:
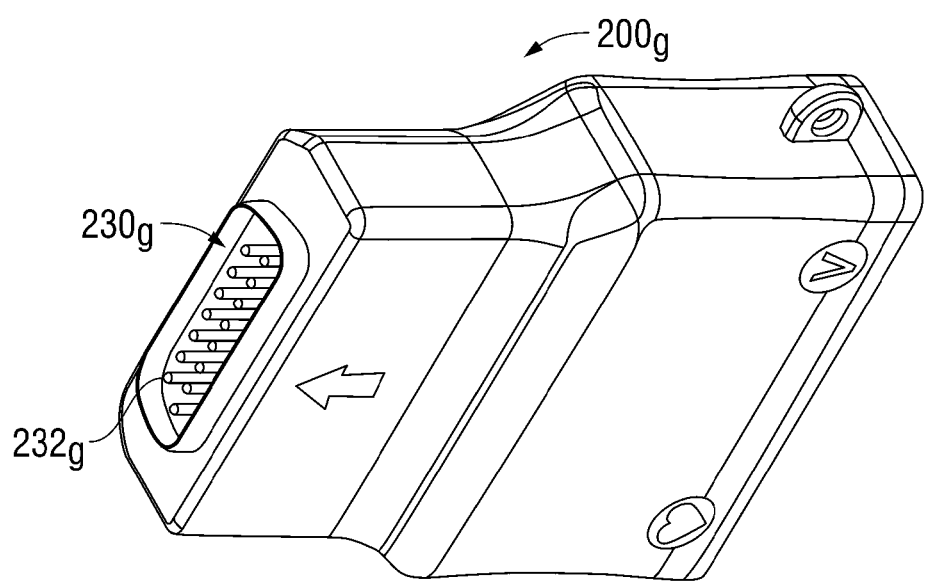

As seen in FIGS. 28 and 29, in another embodiment, adapter $200_g$ includes a pair of input receptacles $220_{g1,g2}$, and a D-Subminiature type (15 pin) monitor plug $230_g$. Adapter $200_g$ may include a resistor element electrically interposed between contact receptacles $222_g$ of each input receptacle $220_g$ and the male contact pins $232_g$ of monitor plug $230_g$. In this embodiment, not all of the male contact pins $232_g$ of monitor plug $230_g$ are connected to a contact receptacle $222_g$ of input receptacles $220_{g1,g2}$.

Figure 30:
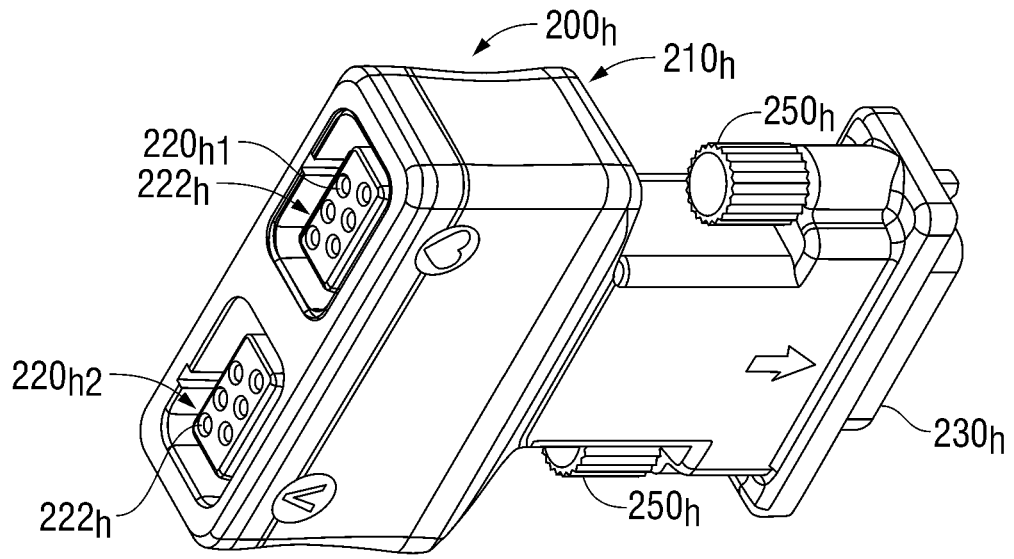
FIGS. 30 and 31 illustrate still another particular embodiment of the adapter of FIGS. 8-10.
Figure 31:
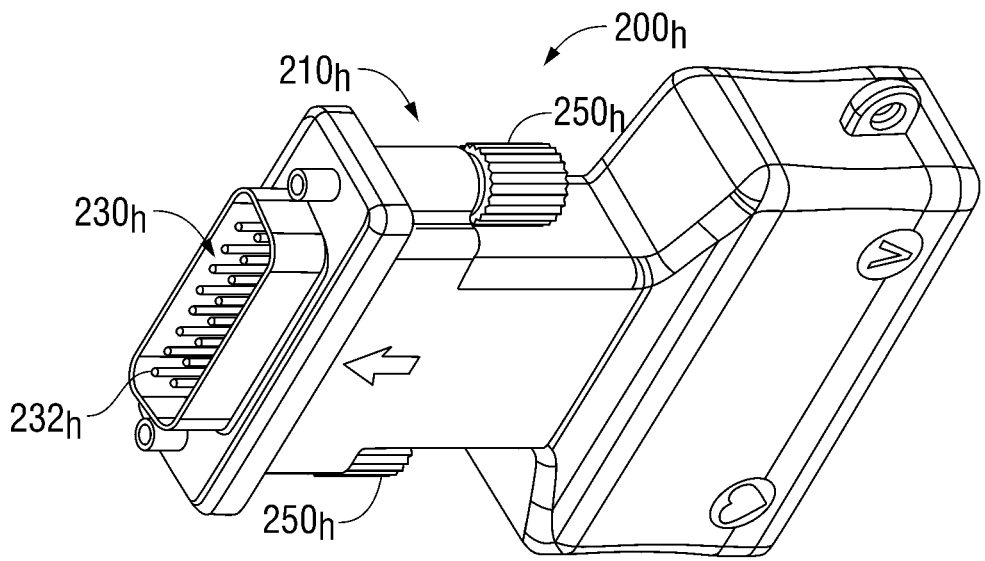
Figure 32:
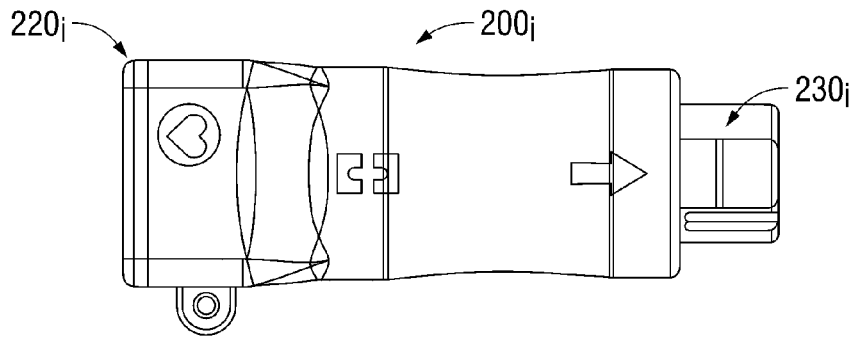
FIGS. 32-34 illustrate yet another particular embodiment of the adapter of FIGS. 8-10.
Figure 33:
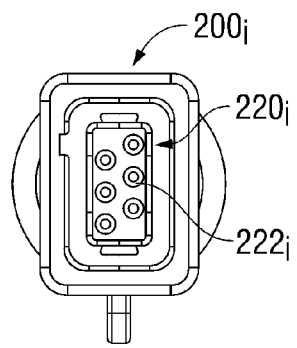
Figure 34:
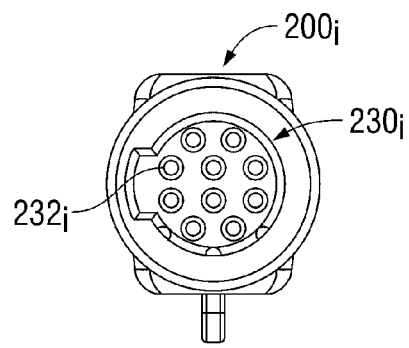
Figure 35:
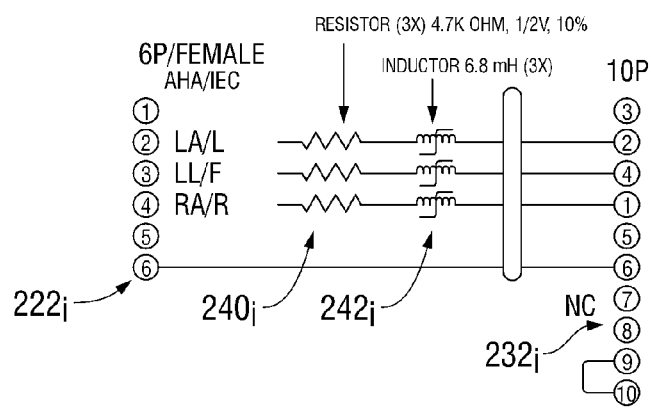
FIGS. 35 and 36 are schematic illustrations of circuits for use in the adapter of FIGS. 32-34.

As seen in FIGS. 30 and 31, in yet another embodiment, adapter $200_h$ includes a pair of input receptacles $220_{h1,h2}$, and a D-Subminiature HP Pagewriter type (15 pin) monitor plug $230_h$. Adapter $200_h$ may include a resistor element electrically interposed between contact receptacles $222_h$ of each input receptacle $220_h$ and the male contact pins $232_h$ of monitor plug $230_h$. In this embodiment, not all of the male contact pins $232_h$ of monitor plug $230_h$ are connected to a contact receptacle $222_h$ of input receptacles $220_{h1,h2}$.

As seen in FIGS. 30 and 31, adapter $200_h$ includes a pair of thumb screws $250_h$ extending through adapter body $210_h$ and located on opposed sides of monitor plug $230_h$. Thumb screws $250_h$ function to secure adapter $200_h$ to the housing of ECG floor monitor 10 when monitor plug $230_h$ is input connector 12 of ECG floor monitor 10.

As seen in FIGS. 32-35, in one embodiment, an adapter $200_i$ includes a single input receptacle $220_i$, and a DATEX type (10 pin) monitor plug $230_i$. As seen in the schematic in FIG. 35, adapter $200_i$ includes a respective resistor and inductor element $240_i$, $242_i$ electrically interposed between each of three contact receptacles $222_i$ of input receptacle $220_i$ and each of three male contact pins $232_i$ of monitor plug $230_i$ thereby making adapter $200_i$ a 3-Lead adapter. In this embodiment, not all of the male contact pins $232_i$ of monitor plug $230_i$ need to be connected to the contact receptacles $222_i$ of input receptacle $220_i$.

Figure 36:
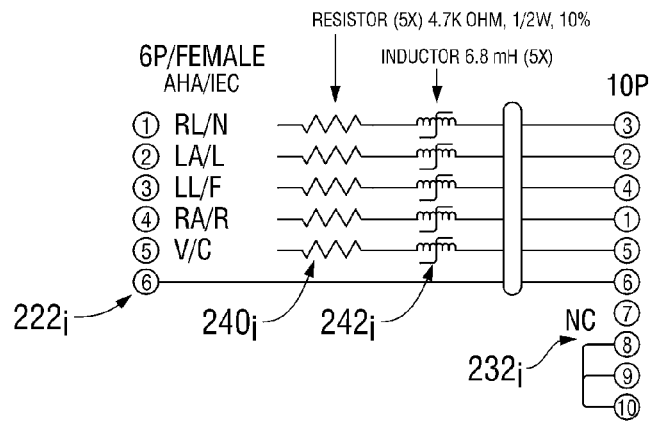
Figure 37:
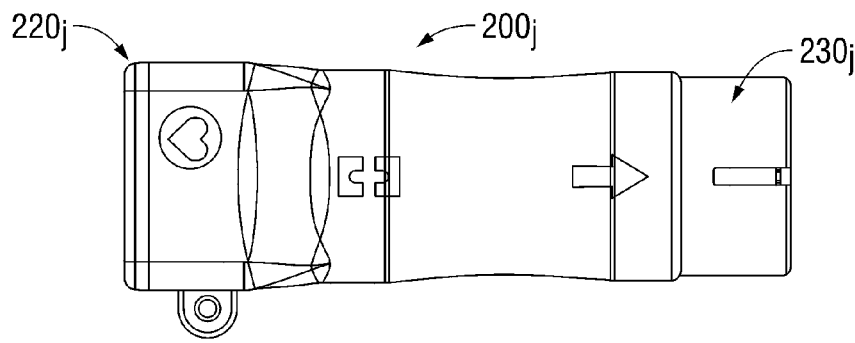
FIGS. 37-39 illustrate a further particular embodiment of the adapter of FIGS. 8-10.
Figure 38:
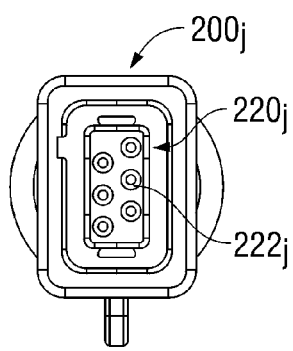
Figure 39:
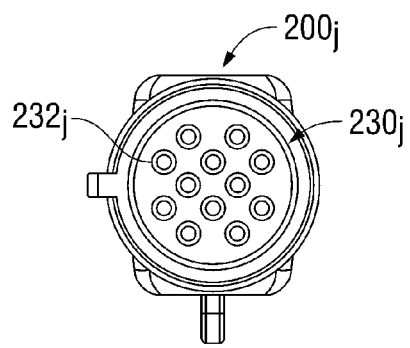
Figure 40:
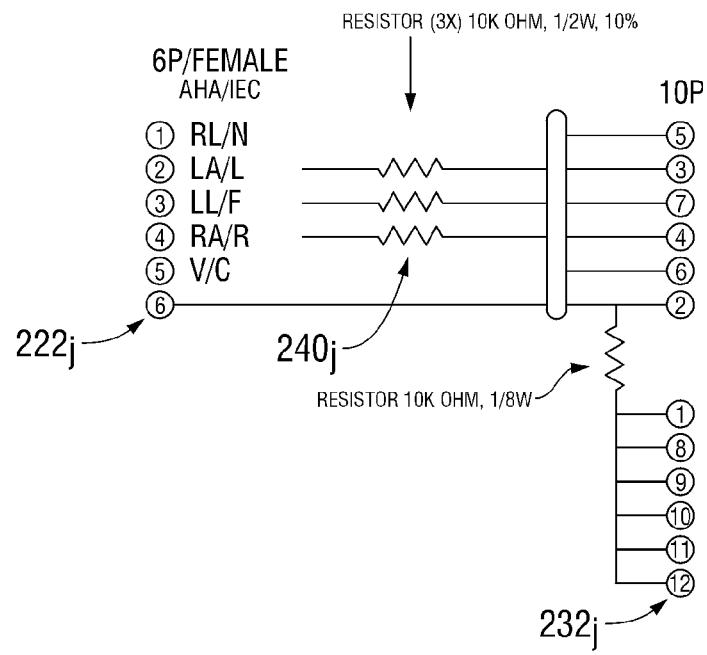
FIGS. 40 and 41 are schematic illustrations of circuits for use in the adapter of FIGS. 37-39.

As seen in the schematic in FIG. 36, in another embodiment, adapter $200_i$ includes a respective resistor and inductor element $240_i$, $242_i$ electrically interposed between each of five contact receptacles $222_i$ of input receptacle $220_i$ and each of five male contact pins $232_i$ of monitor plug $230_i$ thereby making adapter $200_i$ a 5-Lead adapter. In this embodiment, not all of the male contact pins $232_i$ of monitor plug $230_i$ need to be connected to the contact receptacles $222_i$ of input receptacle $220_i$.

As seen in FIGS. 37-41, in one embodiment, adapter $200_j$ includes a single input receptacle $220_j$, and a MEDTRONIC type (12 pin) monitor plug $230_j$. As seen in the schematic in FIG. 40, adapter $200_j$ includes a respective resistor element $240_j$ electrically interposed between each of three contact receptacles $222_j$ of input receptacle $220_j$ and each of three male contact pins $232_j$ of monitor plug $230_j$ thereby making adapter $200_j$ a 3-Lead adapter. In this embodiment, not all of the male contact pins $232_j$ of monitor plug $230_j$ need to be connected to the contact receptacles $222_j$ of input receptacle $220_j$.

Figure 41:
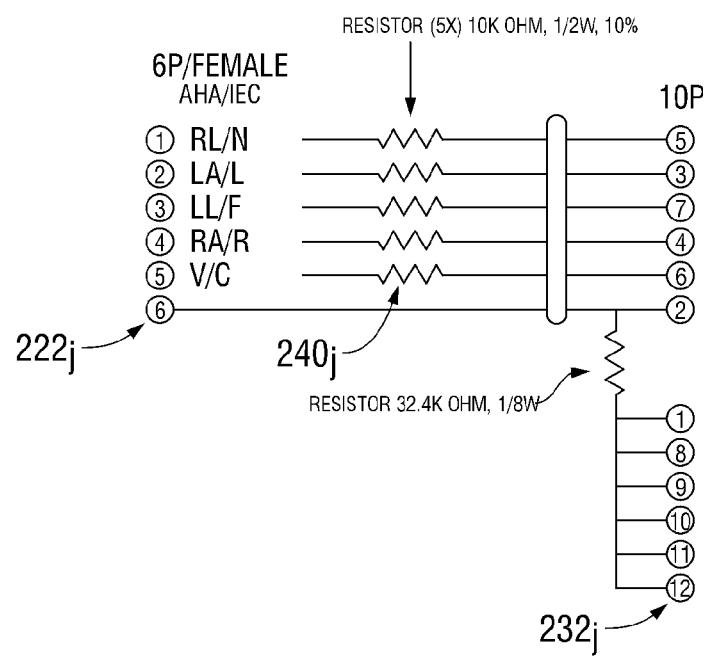
Figure 42:
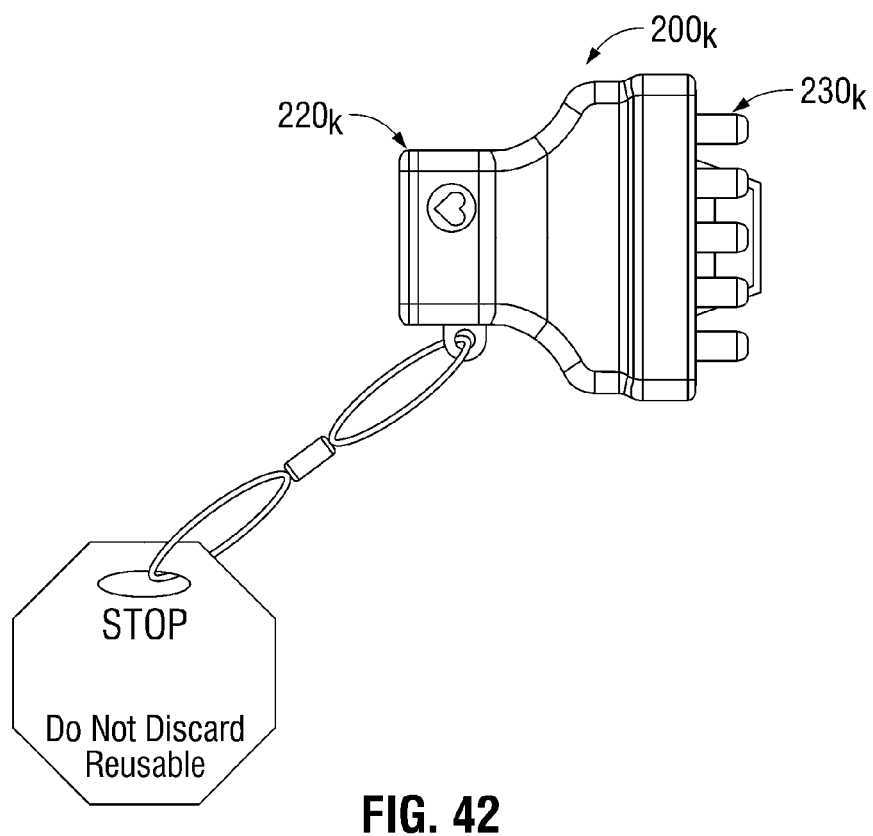
FIGS. 42-46 illustrate a further particular embodiment of the adapter of FIGS. 8-10.
Figure 43:
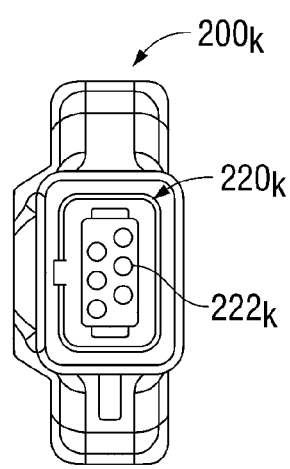
Figure 44:
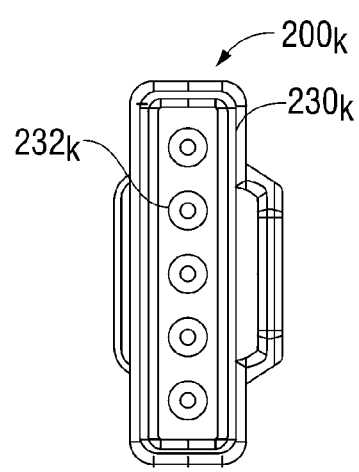
Figure 45:
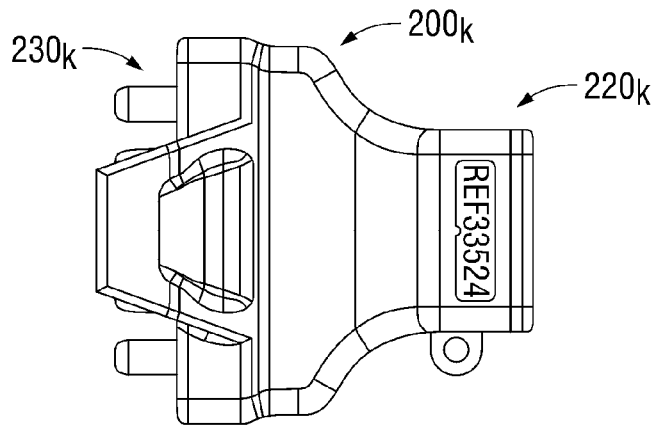
Figure 46:
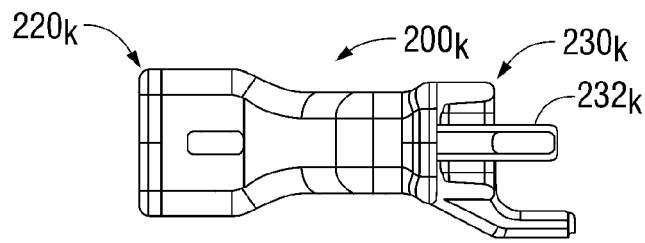
Figure 47:
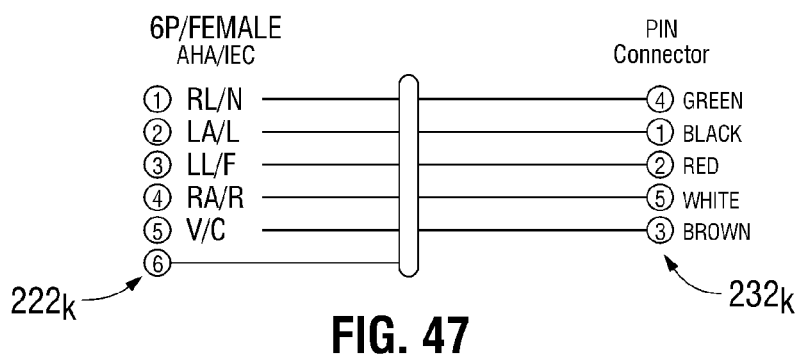
FIG. 47 is a schematic illustrations of a circuit for use in the adapter of FIGS. 42-46.

As seen in the schematic in FIG. 41, in another embodiment, adapter $200_j$ includes a respective resistor element $240_j$ electrically interposed between each of five contact receptacles $222_j$ of input receptacle $220_j$ and each of five male contact pins $232_j$ of monitor plug $230_j$ thereby making adapter $200_j$ a 5-Lead adapter. In this embodiment, not all of the male contact pins $232_j$ of monitor plug $230_j$ need to be connected to the contact receptacles $222_j$ of input receptacle $220_j$.

As seen in FIGS. 42-47, in an embodiment, an adapter $200_k$ includes a single input receptacle $220_k$, and a SPACELABS Dual Connect type (5 pin) monitor plug $230_k$. As seen in the schematic in FIG. 47, only five of the six contact receptacles $222_k$ of input receptacle $220_k$ are used and connected to specific ones of the five contact pins $232_k$ of monitor plug $230_k$.

Turning now to FIG. 48, ECG lead system 100 is shown and includes a ECG lead extension assembly 400 configured and adapted to interconnect ECG lead set assembly 300 to any one of a number of adapters $200_x$, when ECG lead set assembly 300 is to be connected to ECG floor monitor 10. As seen in FIG. 48, ECG lead extension assembly 400 includes a lead extension cable 402, a device connector 410 at one end of the lead extension cable 402 and an ECG lead set assembly connector 420 at the other end of the lead extension cable 402. Lead extension cable 402 includes a plurality of encased and insulated wires disposed in side by side relation. Insulated wires 304 may be EMI/RF shielded. Lead extension cable 402 is in the form of a ribbon cable configured for transmitting electrical signals.

In accordance with the present disclosure, device connector 410 of ECG lead extension assembly 400 is configured and dimensioned to mate and electrically connect with input receptacle $220_x$ of any one of adapters $200_x$. Meanwhile, ECG lead set assembly connector 420 of ECG lead extension assembly 400 is configured and dimensioned to mate and electrically connect with device connector 310 of any one of ECG lead set assemblies 300.

It is contemplated that ECG lead extension assembly 400 may have a length of approximately 7.0' (2.1 m) to approximately 10.0' (3.1 m). In an embodiment, ECG lead extension assembly 400 may have a length of approximately 9.0' (3.0 m). In this manner, with ECG lead set assembly 300 having a length of approximately 3.0' (1.0 m), the overall length of ECG lead set assembly 300 and ECG lead extension assembly 400 may be approximately 10.0' (3.1 m) to approximately 13.0' (4.1 m), preferably approximately 12.0' (4.0 m).

With continued reference to FIG. 48, ECG lead system 100 includes an ECG telemetry adapter 500 configured and adapted to interconnect ECG lead set assembly 300 to ECG telemetry monitor 20. ECG telemetry adapter 500 includes an adapter body 510, at least one input receptacle 520 disposed on one side of adapter body 510, and a telemetry plug 530 disposed on another side of adapter body 510. Each input receptacle 520 is configured to electrically mate with device connector 310 of any one of ECG lead set assemblies 300.

In particular, input receptacle 520 is in the form of an AAMI type (6 pin) plug, and telemetry plug 530 is in the form of a GE 5 prong, 10 pin telemetry plug that is configured and adapted to mate with and electrically connect to ECG telemetry monitor 20.

With continued reference to FIG. 48, in use, when a patient is in, for example, the emergency room (ER), the operating room (OR), the post-anesthesia care unit (PACU), the intensive care unit (ICU) and/or the critical care unit (CCU), the patient is typically connected to ECG floor monitor 10. In particular, the patient is connected to an ECG lead set assembly 300 via electrodes or the like (not shown), the ECG lead set assembly 300 is mated with and electrically connected to ECG lead extension assembly 400 (as described above), ECG lead extension assembly 400 is mated with and electrically connected to an appropriate one of any number of adapters 200$_X$ (as described above), and the appropriate adapter is mated with and electrically connected to ECG floor monitor 10. The use of the ECG lead extension assembly 400 is desired since the location of the patient wearing the ECG lead set assembly 300 is typically remote from the location of the ECG floor monitor 10 and since the use of telemetry in these fields is undesirable and/or not recommended.

Following the patients stay in the emergency room (ER), the operating room (OR), the post-anesthesia care unit (PACU), the intensive care unit (ICU) and/or the critical care unit (CCU), if and/or when the patient is transferred to a telemetry floor for monitoring, the need for ECG lead extension assembly 400 may no longer be necessary if the patient is to be connected to ECG telemetry monitor 20. As such, ECG lead extension assembly 400 may be removed and the ECG lead set assembly 300 mated with and electrically connected to an ECG telemetry adapter 500 (as described above). The ECG telemetry adapter 500 is then mated with and electrically connected to ECG telemetry monitor 20. The need for the ECG lead extension assembly 400 is no longer necessary since the patient wearing the ECG lead set assembly 300 is typically also carrying of otherwise wearing the ECG telemetry monitor 20.

In this manner, the same ECG lead set assembly 300 may be used for the emergency room (ER), the operating room (OR), the post-anesthesia care unit (PACU), the intensive care unit (ICU) and/or the critical care unit (CCU), and for the telemetry floor. As can be appreciated only the ECG lead extension assembly 400 need to be disposed of at this time.

It is contemplated that ECG lead set assembly 300 and/or ECG lead extension assembly 400 may be provided with a latching system for reducing any incidences of inadvertent and/or undesired disconnection of device connector 310 of any one of ECG lead set assemblies 300 from ECG lead set assembly connector 420 of ECG lead extension assembly 400. Exemplary latching systems will now be shown and described with reference to FIGS. 43A-51B.

Figure 49A:
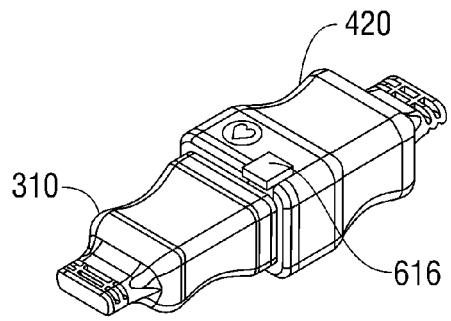
FIGS. 49A-49c illustrate a latching system, according to an embodiment of the present disclosure, for use with the ECG lead system of the present disclosure.
Figure 49B:
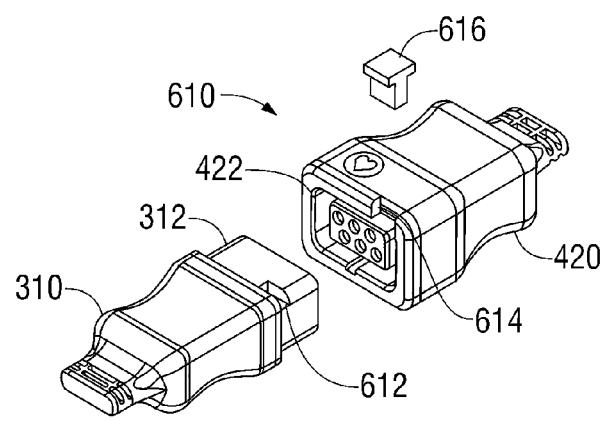
Figure 49C:
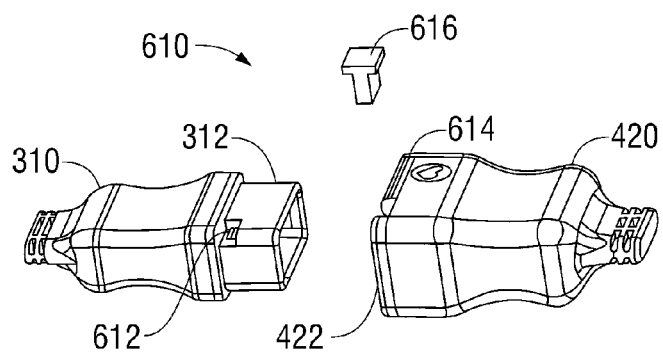

As seen in FIGS. 49A-49C, a latching system 610 for device connector 310 of any one of ECG lead set assemblies 300 and ECG lead set assembly connector 420 of ECG lead extension assembly 400 is provided. Latching system 610 includes a recess 612 formed in perimeteral wall 312 of device connector 310, and a recess 614 formed in a perimeteral wall 422 of ECG lead set assembly connector 420. Recesses 612 and 614 are configured and located so as to align with one another and come into registration with one another when device connector 310 is connected to ECG lead set assembly connector 420.

Latching system 610 further includes a removable locking tab 616 configured to extend through and between recesses 612 and 614 of device connector 310 and ECG lead set assembly connector 420, respectively. In use, following connection of device connector 310 to ECG lead set assembly connector 420, locking tab 616 is inserted into recesses 612 and 614 thereby securing device connector 310 and ECG lead set assembly connector 420 to one another.

Figure 50A:
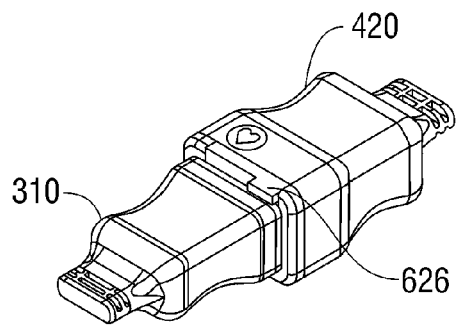
Figure 50B:
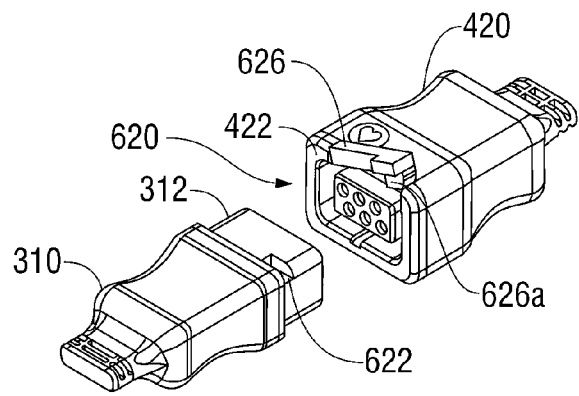
Figure 50C:
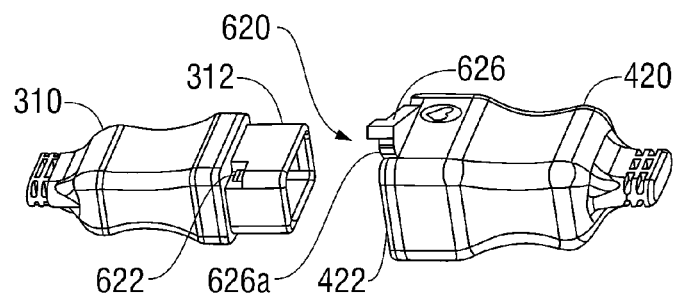

Turning now to FIGS. 50A-50C, a latching system 620 according to another embodiment is provided. Latching system 620 includes a recess 622 formed in perimeteral wall 312 of device connector 310, and a latch arm 626 pivotally connected to perimeteral wall 422 of ECG lead set assembly connector 420. Latch arm 626 includes an open position permitting connection and disconnection of device connector 310 and ECG lead set assembly connector 420 to/from one another. Latch arm 626 further includes a closed position preventing disconnection of device connector 310 and ECG lead set assembly connector 420 from one another. In the closed position, a tab 626a of latch arm 626 extends into recess 622 formed in perimeteral wall 312 of device connector 310.

Figure 51A:
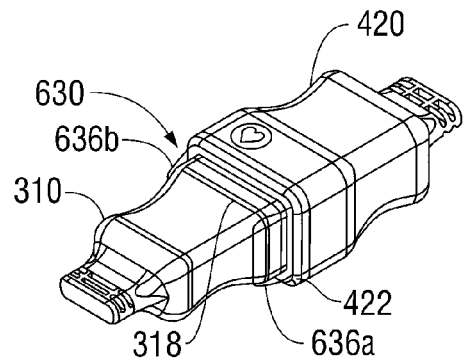
FIGS. 51A-51c illustrate a latching system, according to yet another embodiment of the present disclosure, for use with the ECG lead system of the present disclosure.
Figure 51B:
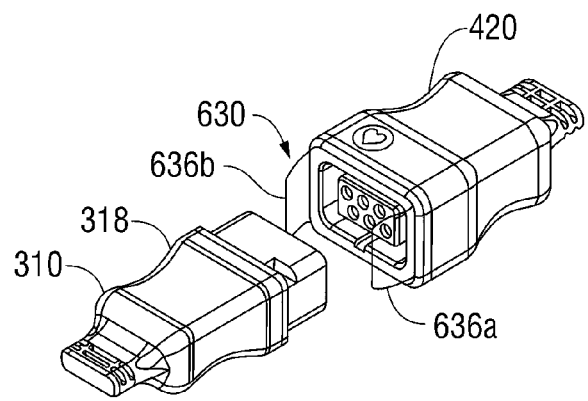
Figure 51C:
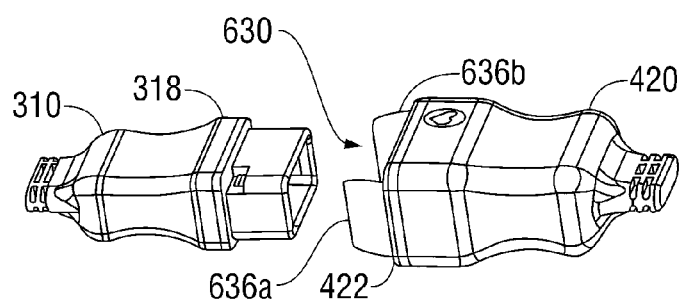

Turning now to FIGS. 51A-51C, a latching system 630 according to yet another embodiment is provided. Latching system 630 includes a pair of resilient flaps 636a, 636b extending distally from side edges of perimeteral wall 422 of ECG lead set assembly connector 420. Flaps 636a, 636b tend to angle toward one another. In this manner, in use, when device connector 310 and ECG lead set assembly connector 420 are connected to one another, flaps 636a, 636b extend over and beyond a neck portion 318 of device connector 310. As such, a force required to disconnect device connector 310 from ECG lead set assembly connector 420 is increased.

Figure 52A:
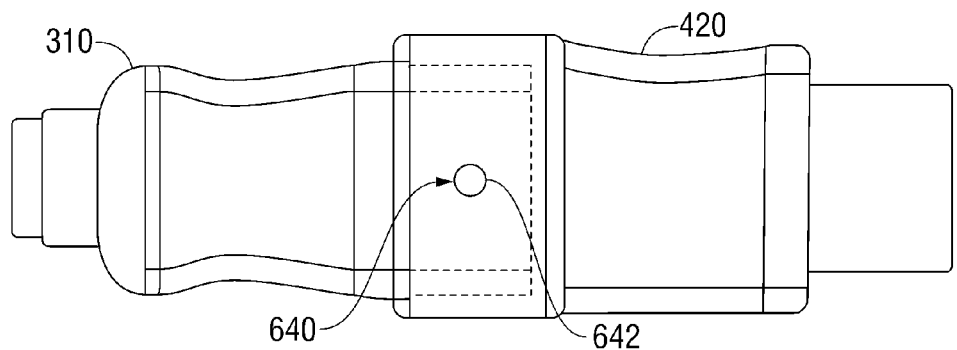
FIGS. 52A-52B illustrate a latching system, according to still another embodiment of the present disclosure, for use with the ECG lead system of the present disclosure.
Figure 52B:
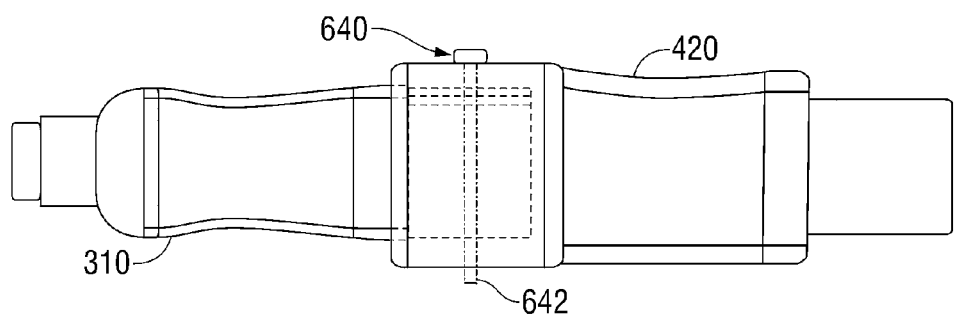

Turning now to FIGS. 52A-52B, a latching system 640 according to still another embodiment is provided. Latching system 640 includes a pin 642 configured and adapted to extend at least partially into and between device connector 310 and ECG lead set assembly connector 420, when device connector 310 and ECG lead set assembly connector 420 are connected to one another.

Figure 53A:
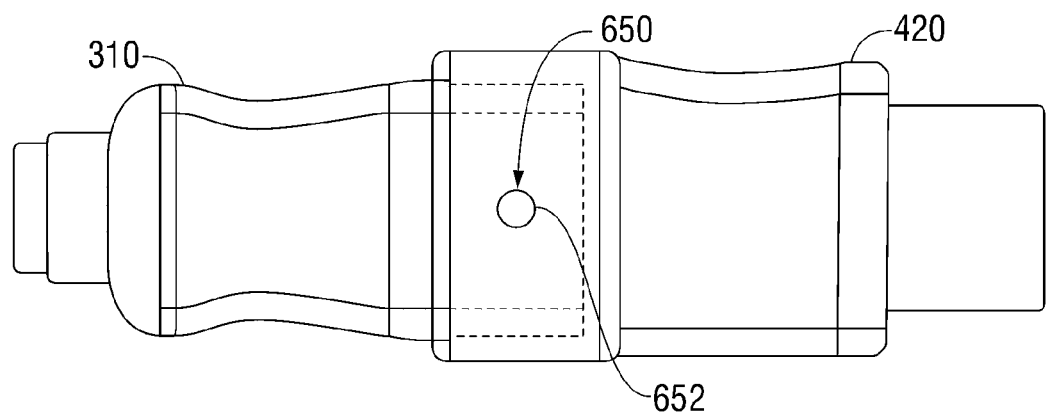
FIGS. 53A-53B illustrate a latching system, according to a further embodiment of the present disclosure, for use with the ECG lead system of the present disclosure.
Figure 53B:
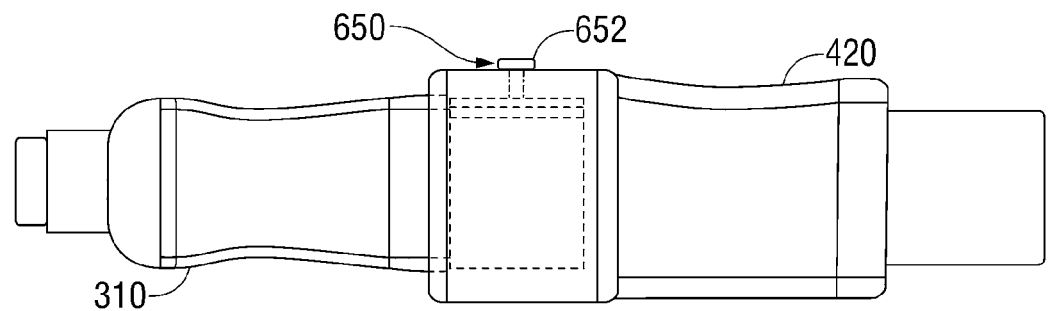

With reference to FIGS. 53A-53B, a latching system 650 according to another embodiment is provided. Latching system 650 includes a lock button 652 supported on ECG lead set assembly connector 420 and being configured and adapted to extend at least partially into and between device connector 310 and ECG lead set assembly connector 420, when device connector 310 and ECG lead set assembly connector 420 are connected to one another.

Figure 54:
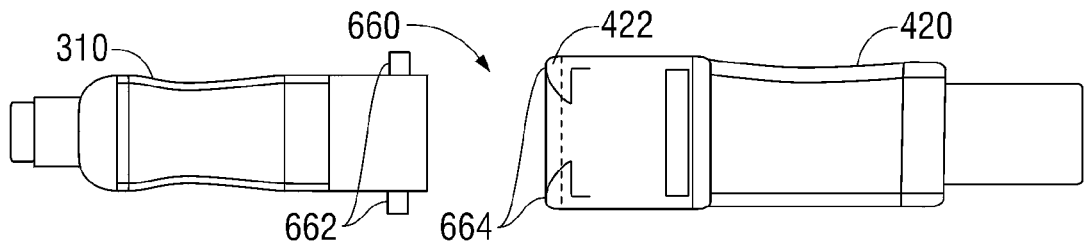
FIG. 54 is a schematic illustration of a latching system, according to another embodiment of the present disclosure, for use with the ECG lead system of the present disclosure.

Turning now to FIG. 54, a latching system 660 according to another embodiment is provided. Latching system 660 includes a pair of tabs 662 extending from an outer surface of device connector 310, and a complementary pair of fingers 664 extending from perimeteral wall 422 of ECG lead set assembly connector 420. Tabs 662 and fingers 664 are configured and dimensioned to snap-fit engage with one another upon the connection of device connector 310 and ECG lead set assembly connector 420 to one another.

Figure 55:
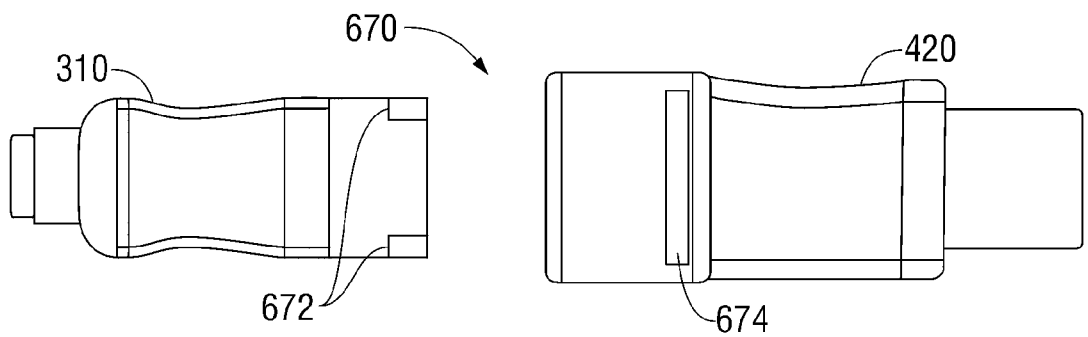
FIG. 55 is a schematic illustration of a latching system, according to yet another embodiment of the present disclosure, for use with the ECG lead system of the present disclosure.

Turning now to FIG. 55, a latching system 670 according to another embodiment is provided. Latching system 670 includes at least one magnet 672 supported in device connector 310, and a complementary at least one magnet supported in ECG lead set assembly connector 420. Magnets 672, 674 are disposed within respective device connector 310 and ECG lead set assembly connector 420 so as to be in magnetic contact with one another when device connector 310 and ECG lead set assembly connector 420 are connected to one another.

Figure 56:
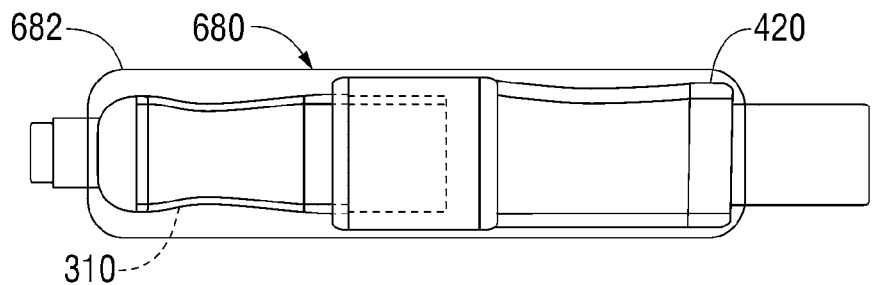
FIG. 56 is a schematic illustration of a latching system, according to still another embodiment of the present disclosure, for use with the ECG lead system of the present disclosure.

Turning now to FIG. 56, a latching system 680 according to another embodiment is provided. Latching system 680 includes a shrink wrap 682 configured and dimensioned to at least partially surround device connector 310 and ECG lead set assembly connector 420 when device connector 310 and ECG lead set assembly connector 420 are connected to one another.

Figure 57A:
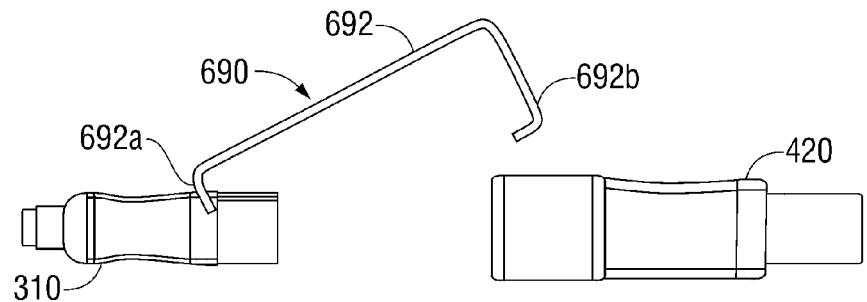
FIGS. 57A-57C illustrate a latching system, according to a further embodiment of the present disclosure, for use with the ECG lead system of the present disclosure.
Figure 57B:
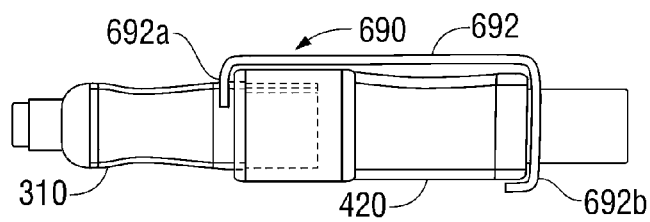
Figure 57C:
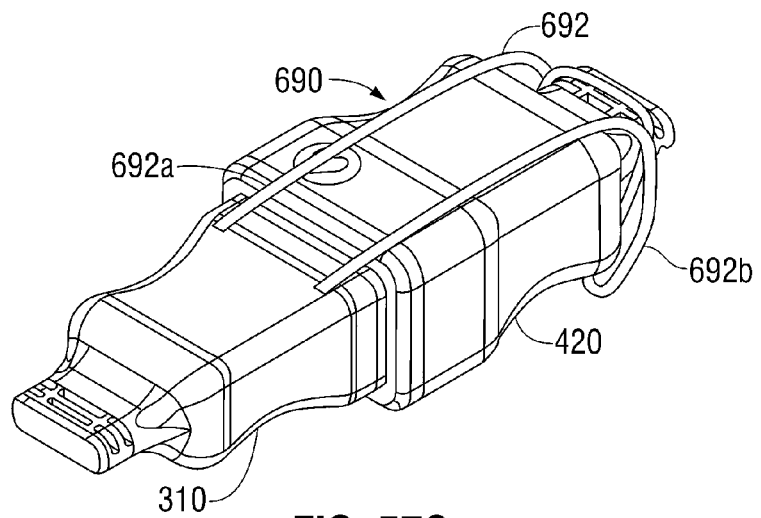

Turning now to FIGS. 57A-57C, a latching system 690 according to another embodiment is provided. Latching system 690 includes a latch clip 692 having a proximal end 692a supported on and extending from device connector 310 and a distal end 692b sufficient spaced from proximal end 692a so as to be disposed behind ECG lead set assembly connector

420, when device connector 310 and ECG lead set assembly connector 420 are connected to one another.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrocardiograph (ECG) lead system for use with an ECG floor monitor or an ECG telemetry monitor, the ECG lead system comprising:
   an ECG lead set assembly, comprising:
      an ECG lead set cable;
      a plurality of electrode connectors disposed at a first end of the ECG lead set cable, wherein the electrode connectors are configured to electrically connect to electrodes placed on a patient; and
      a device connector disposed at a second end of the ECG lead set cable and configured to directly mate with, in a first configuration, an ECG lead set assembly connector of an ECG lead extension cable and, in a second configuration, an input receptacle of an ECG telemetry monitor adapter;
   the ECG lead extension assembly, comprising:
      an ECG lead extension cable;
      the ECG lead set assembly connector disposed at a first end of the ECG lead extension cable, wherein the ECG lead set assembly connector is configured and adapted to directly mate and electrically connect to the device connector of the ECG lead set assembly; and
      a device connector disposed at a second end of the ECG lead extension cable;
   an ECG floor monitor adapter, comprising:
      an input receptacle adapted and configured to directly mate with and electrically connect to the device connector of the ECG lead extension assembly; and
      an ECG floor monitor plug electrically connected to the input receptacle, the ECG floor monitor plug adapted and configured to directly mate with and electrically connect to a corresponding receptacle of an ECG floor monitor; and
   the ECG telemetry monitor adapter, including:
      the input receptacle adapted and configured to directly mate with and electrically connect to the device connector of the ECG lead set assembly; and
      an ECG telemetry monitor plug electrically connected to the input receptacle, the ECG telemetry monitor plug adapted and configured to directly mate with and electrically connect to a corresponding receptacle of an ECG telemetry monitor.

2. The ECG lead system according to claim 1, wherein each electrode connector includes:
   a housing defining an aperture therein;
   a lead wire terminal disposed within the housing and accessible through the aperture of the housing, wherein the lead wire terminals are electrically connectable to the electrodes placed on the patient;
   a contact plate electrically connected to the lead wire terminal, the contact plate defines a keyhole slot that is in registration with the aperture of the housing, the keyhole slot includes a first slot portion and a second slot portion, wherein the first slot portion has an internal diameter which is greater than an internal diameter of the second slot portion; and
   a lever pivotably connected to the housing and is biased to a first position, wherein the lever includes a cam finger projecting therefrom so as to extend across the first slot portion of the keyhole slot when the lever is in the first position.

3. The ECG lead system according to claim 2, wherein the lever is actuatable to a second position wherein the cam finger does not extend across the first slot portion of the keyhole slot.

4. The ECG lead system according to claim 2, wherein each electrode connector includes a biasing member disposed within the housing and operatively engaged with the lever to bias the lever to the first position.

5. The ECG lead system according to claim 1, further comprising a latching system for increasing a disconnection force required to disconnect the device connector of the ECG lead set cable and the ECG lead set assembly connector of the ECG lead extension assembly.

6. The ECG lead system according to claim 5, wherein the latching system includes a locking tab insertable into a recess of the device connector of the ECG lead set cable and a recess of the ECG lead set assembly connector of the ECG lead extension assembly, wherein the recesses are in registration with one another when the device connector of the ECG lead set cable and the ECG lead set assembly connector of the ECG lead extension assembly are connected to one another.

7. The ECG lead system according to claim 5, wherein the latching system includes a latch arm pivotably connected to the device connector of the ECG lead set cable, wherein the latch arm is pivotable to a closed position wherein a tab extending therefrom is inserted into a recess defined in a surface of the ECG lead set assembly connector of the ECG lead extension assembly.

8. The ECG lead system according to claim 5, wherein the latching system includes a pair of resilient flaps extending distally from opposed side edges of the device connector of the ECG lead set cable, wherein pair of resilient flaps project toward one another, and wherein the pair of flaps overlie a surface of the ECG lead set assembly connector of the ECG lead extension assembly when the ECG lead set assembly connector is connected to the device connector of the ECG lead set cable.

9. The ECG lead system according to claim 1, wherein at least one of the ECG floor monitor plug and the ECG telemetry monitor plug has a configuration selected from the group consisting of an AAMI type (6 pin) configuration, a GE/Marquette type (11 pin) configuration, a Philips type (12 pin) configuration, a HP type (8 pin) configuration, a Spacelabs type (17 pin) configuration, a D-Subminiature type (15 pin) configuration, a D-Subminiature HP Pagewriter type (15 pin) configuration, a Datex type (10 Pin) configuration, a Medtronic type (12 pin) configuration, and a Spacelabs Dual Connect type (5 pin) configuration.

10. A method of connecting a patient to any of a plurality of unique diverse electrocardiograph (ECG) floor monitors for when a patient is substantially immobile or any of a plurality of unique diverse ECG telemetry monitors, the method comprising:
   providing an ECG lead system, the ECG lead system including:
      an ECG lead set assembly including an ECG lead set cable having a plurality of electrode connectors disposed at a first end of the ECG lead set cable and a device connector disposed at a second end of the ECG lead set cable and configured to directly mate with, in a first configuration, an ECG lead set assembly connector of an ECG lead extension cable and, in a second configuration, an input receptacle of an ECG telemetry monitor adapter;

the ECG lead extension assembly including an ECG lead extension cable having the ECG lead set assembly connector disposed at a first end and a device connector disposed at a second end;

a plurality of unique adapters, wherein
at least one of the plurality of unique adapters includes an input receptacle configured for selective electrical connection with a device connector of the ECG lead extension cable; and a unique ECG floor monitor plug electrically connected to the input receptacle, the unique ECG floor monitor plug configured to selectively electrically connect to a corresponding receptacle of a respective unique diverse ECG floor monitor; and, wherein
at least one of the adapters includes an input receptacle configured for selective electrical connection with the device connector of the ECG lead set assembly and a unique ECG telemetry monitor plug electrically connected to the input receptacle, the unique ECG telemetry monitor plug configured to selectively electrically connect to a corresponding receptacle of a respective unique diverse ECG telemetry monitor;

determining whether an ECG floor monitor or an ECG telemetry monitor is to be used;

determining the type of ECG floor monitor or ECG telemetry monitor to be used;

selecting an adapter from the plurality of unique adapters that corresponds to the type of ECG floor monitor or ECG telemetry monitor to be used; and when an ECG floor monitor is used, then:
directly connecting the device connector of the ECG lead set assembly to the device connector of the ECG lead extension cable;
directly connecting the device connector of the ECG lead extension cable to the input receptacle of the selected adapter; and
directly connecting the unique ECG floor monitor plug to a corresponding receptacle of the ECG floor monitor being used: and when an ECG telemetry monitor is used, then:
directly connecting the device connector of the ECG lead set assembly to the input receptacle of the selected adapter; and
directly connecting the unique ECG telemetry monitor plug to a corresponding receptacle of the ECG telemetry monitor being used.

11. An electrocardiograph (ECG) lead system for use with an ECG monitoring system, comprising:
a lead set assembly, including:
a lead cable;
a plurality of electrode connectors disposed along a first end of the lead cable configured to electrically connect to a plurality of electrodes disposed on a patient; and
a device connector disposed along a second end of the lead cable and configured to directly mate with, in a first configuration, a lead set assembly connector of an extension cable and, in a second configuration, an input receptacle of a lead adapter connector;
the extension cable including:
the lead set assembly connector disposed at a first end of the extension cable, the lead set assembly connector configured to directly electrically connect to the device connector of the lead set assembly; and
a lead adapter connector disposed at a second end of the extension cable; and
a lead adapter, including:
an adapter body;
an input receptacle disposed along a first end of the adapter body, wherein the input receptacle is configured to directly electrically connect to the device connector of the lead set assembly when the extension cable is not used and wherein the input receptacle is configured to electrically connect to the lead adapter connector of the extension cable when the extension cable is used; and
an output receptacle disposed along second end of the adaptor body, wherein the output receptacle is configured to electronically connect to the ECG monitoring system.

12. The ECG lead system of claim 11, wherein the output receptacle of the lead adapter is configured to electronically connect to at least one of an ECG floor monitor and an ECG telemetry monitor.

13. The ECG lead system of claim 12, wherein the extension cable is configured to be connected between the device connector of the lead set assembly and the input receptacle of the adapter body when the device connector of the adaptor body is electrically connected to the ECG floor monitor.

14. The ECG lead system of claim 12, wherein the device connector of the lead set assembly is configured to directly electrically connect to the input receptacle of the adapter body when the device connector of the adaptor body is electrically connected to the ECG telemetry monitor.

15. The ECG lead system of claim 11, wherein the input receptacle of the lead adaptor is one of a single and a pair of input receptacles.

16. The ECG lead system of claim 11, wherein the output receptacle of the lead adaptor is selected from the group consisting of a AAMI type (6 pin) plug, a GE/Marquette type (11 pin) plug, a Philips type (12 pin) plug, a HP type (8 pin) plug, a Spacelabs type (17 pin) plug, a D-Subminiature type (15 pin) plug, a D-Subminiature HP Pagewriter type (15 pin) plug, a DATEX type (10 pin) plug, and a MEDTRONIC type (12 pin) plug.

17. A ECG lead kit for monitoring ECG data, the kit comprising:
a lead set assembly, including:
a lead cable;
a plurality of electrode connectors disposed along a first end of the lead cable configured to electrically connect to a plurality of electrodes disposed on a patient; and
a device connector disposed along a second end of the lead cable and configured to directly mate with, in a first configuration, a lead set assembly connector of an extension cable and, in a second configuration, an input receptacle of an ECG telemetry monitor adapter in a first configuration and directly mate with the other one of the lead set assembly connector of the extension cable or the input receptacle of the ECG telemetry monitor adapter in a second configuration;
a plurality of ECG telemetry monitor adapters, each ECG telemetry monitor adapter including:
an adapter body;
an input receptacle disposed along a first end of the adaptor body, wherein the input receptacle is configured to directly electrically connect to the device connector of the lead set assembly; and a unique output receptacle disposed along a second end of the adaptor body, wherein the output receptacle is configured to directly electronically connect to a corresponding receptacle of a unique diverse ECG telemetry monitor;

the extension cable, the extension cable including:
the lead set assembly connector disposed at a first end thereof, wherein the lead set assembly connector is configured to mate with and electronically connect to the device connector of the lead set assembly; and
an ECG floor monitor adapter connector disposed at a second end of the thereof; and a plurality of ECG floor monitor adapters, each ECG floor monitor adapter including:
an adapter body;
an input receptacle disposed along a first end of the adaptor body, wherein the input receptacle is configured to directly electrically connect to the ECG floor monitor adapter connector of the extension cable; and
a unique output receptacle disposed along a second end of the adaptor body, wherein the output receptacle is configured to directly electronically connect to a corresponding receptacle of a unique diverse ECG floor monitor.

18. The kit of claim 17, wherein the unique output receptacle of one of the ECG floor monitor adapters or the unique output receptacle of one of the ECG telemetry monitor adapters has a configuration from the group consisting of a AAMI type (6 pin) plug, a GE/Marquette type (11 pin) plug, a Philips type (12 pin) plug, a HP type (8 pin) plug, a Spacelabs type (17 pin) plug, a D-Subminiature type (15 pin) plug, a D-Subminiature HP Pagewriter type (15 pin) plug, a DATEX type (10 pin) plug, and a MEDTRONIC type (12 pin) plug.

* * * * *